US008552032B2

(12) United States Patent
Lawson et al.

(10) Patent No.: US 8,552,032 B2
(45) Date of Patent: Oct. 8, 2013

(54) BICYCLIC DERIVATIVES USEFUL AS INHIBITORS OF DPP-1

(75) Inventors: Edward C. Lawson, Pipersville, PA (US); Dennis J. Hlasta, Doylestown, PA (US); Shyamali Ghosh, Norristown, PA (US); Renee L. DesJarlais, Saint Davids, PA (US); Carsten Schubert, Phoenixville, PA (US)

(73) Assignee: Janssen Pharmaceutica NV (BE)

( * ) Notice: Subject to any disclaimer, the term of this patent is extended or adjusted under 35 U.S.C. 154(b) by 96 days.

(21) Appl. No.: 12/970,247

(22) Filed: Dec. 16, 2010

(65) Prior Publication Data

US 2011/0152321 A1 Jun. 23, 2011

Related U.S. Application Data

(60) Provisional application No. 61/287,911, filed on Dec. 18, 2009.

(51) Int. Cl.

| | |
|---|---|
| *A61K 31/343* | (2006.01) |
| *A61K 31/381* | (2006.01) |
| *A61K 31/404* | (2006.01) |
| *A61K 31/4184* | (2006.01) |
| *C07D 209/04* | (2006.01) |
| *C07D 235/04* | (2006.01) |
| *C07D 307/78* | (2006.01) |
| *C07D 333/52* | (2006.01) |

(52) U.S. Cl.
USPC ........... 514/320; 514/323; 514/394; 514/443; 514/469; 546/196; 546/201; 548/309.7; 548/504; 549/58; 549/467

(58) Field of Classification Search
USPC .......... 549/58, 467; 548/309.7, 504; 546/196, 546/201
See application file for complete search history.

(56) References Cited

U.S. PATENT DOCUMENTS

| | | | |
|---|---|---|---|
| 4,613,676 | A | 9/1986 | Fuhrer et al. |
| 4,719,288 | A | 1/1988 | Fuhrer et al. |
| 4,863,903 | A | 9/1989 | Fuhrer et al. |

FOREIGN PATENT DOCUMENTS

| | | |
|---|---|---|
| EP | 0 143 746 A2 | 11/1984 |
| JP | 10182616 A | 12/1996 |
| WO | WO 93 / 01166 A | 1/1993 |
| WO | WO 94 / 11390 A1 | 5/1994 |
| WO | WO 2004/106289 A1 | 12/2004 |
| WO | WO 2006/094003 A1 | 9/2006 |
| WO | WO 2007 / 038459 A2 | 4/2007 |
| WO | WO 2009 / 023495 A2 | 2/2009 |
| WO | WO 2009/074829 | 6/2009 |
| WO | WO 2009/129371 A1 | 10/2009 |

OTHER PUBLICATIONS

Yoshimura, et al. (Document No. 129:119075), Jul. 13, 1998, retrieved from CAPLUS.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wikilCancer.*
International Search Report, PCTUS2010/060986, dated Mar. 9, 2011.
Methot, N., et al., "In Vivo Inhibition of Serine Protease Processing Requires a High Fractional Inhibition of Cathepsin C", *Molecular Pharmacology* 2008, pp. 1847-1865, vol. 73(6).
Elliott, G.I., et al., "Intramolecular Diels-Alder / 1,3-Dipolar Cycloaddition Cascade of 1,3,4-Oxadiazoles", *J. Am. Chem. Soc.*, 2006, pp. 10589-10595, vol. 128(32).
Kiviranta, P.H., et al., "N-(3-(4-Hydroxyphenyl)-propenoyl)-amino acid tryptamides as SIRT2 inhibitors", *Bioorg. & Med. Chem. Lett.*, 2007, pp. 2448-2451, vol. 17(9).
Kovac, L., et al., "148. Synthetic Analogues of Naturally Occurring Spider Toxins", *Helvetica Chimica Acta*, 1992, pp. 1909-1924, vol. 75(6).
Elliott, et al., "Intramolecular Diels-Alder/1,3-Dipolar Cycloaddition Cascade of 1,3,4-Oxadiazoles", Journal of the Amer9can Chemical Society, Jul. 22, 2006, pp. S-1-S-98, xp002625673.

* cited by examiner

*Primary Examiner* — Shawquia Young
(74) *Attorney, Agent, or Firm* — Mary A. Appollina

(57) ABSTRACT

The present invention is directed to novel bicyclic derivatives, pharmaceutical compositions containing them and their use in the treatment of disorders and conditions modulated by DPP-1.

24 Claims, No Drawings

BICYCLIC DERIVATIVES USEFUL AS INHIBITORS OF DPP-1

CROSS-REFERENCE TO RELATED APPLICATIONS

This application claims priority from U.S. Provisional Application Ser. Nos. 61/287,911 filed Dec. 18, 2009, the contents of each of which are hereby incorporated by reference in their entirety.

FIELD OF THE INVENTION

The present invention is directed to novel bicyclic derivatives, pharmaceutical compositions containing them and their use in the treatment of disorders and conditions modulated by DPP-1.

BACKGROUND OF THE INVENTION

Chronic Obstructive Pulmonary Disease (COPD) is characterized by the progressive development of irreversible airflow limitation. COPD consists of chronic obstructive bronchitis, with obstruction of small airways, and emphysema, with enlargement of air spaces and destruction of lung parenchyma, loss of lung elasticity, and closure of small airways. In COPD patients, there were increased numbers of neutrophils, cytotoxic T lymphocytes and macrophages in bronchioalveolar lavage (BAL) airways and lung parenchyma. The presence of these inflammatory cells is correlated well with severity of airway obstruction and alveolar wall destruction. It has been shown that neutrophil elastase; cathepsin G and proteinase 3 can produce emphysema and mucus hypersecretion in lab animals. Granzymes A & B are the neutral serine proteases that are expressed exclusively in the granules of activated cytotoxic T lymphocytes. In COPD the protease-antiprotease balance appears to be tipped in favor of increased proteolysis due to increase in polymorphonuclear neutrophil (PMN)-derived proteases, cathepsins and matrix metalloproteases (MMPs). Therefore, a drug that inhibits all or most of the relevant proteases mentioned above is expected to be effective in the treatment of COPD.

Dipeptidyl Peptidase-1 (DPP-1, cathepsin C) is a member of the lysosomal papain-type cysteine protease family that also includes cathepsin B, K, H, L, O, and S. DPP-1 (MW 200 kd) is composed of a dimer of disulfide-linked heavy and light chains, both from a single protein precursor. DPP-1 mRNA is highly expressed in tissues such as lung, spleen, kidney and liver; in inflammatory cells such as PMN, cytotoxic T lymphocytes, alveolar macrophages and mast cells. The biological function of DPP-1 is to convert inactive proenzymes into active enzyme by removing a dipeptide from N-terminal. The proenzymes that are activated by DPP-1 are PMN-derived proteases, granzymes A & B, chymase and tryptase. Since these enzymes play an important pathological role in COPD, inhibition of DDP-1 by small molecules would be a rational therapeutic intervention for COPD. Additional therapeutic indications for a DPP-1 inhibitor are asthma, rhinitis, and rheumatoid arthritis.

There remains a need for inhibitors of DPP-1 for the treatment of DPP-1 mediated disorders and conditions, including but not limited to rheumatoid arthritis, asthma, chronic obstructive pulmonary disease, sepsis, irritable bowel disease, cystic fibrosis, and abdominal aortic aneurism.

SUMMARY OF THE INVENTION

The present invention is directed to compounds of formula (I)

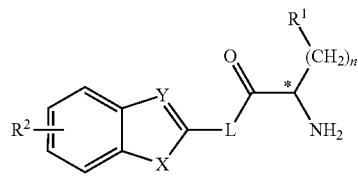

wherein $R^1$ is selected from the group consisting of $C_{1-4}$alkyl, —C(O)—$NH_2$, $C_{3-6}$cycloalkyl, phenyl and 5 to 6 membered heteroaryl; wherein the heteroaryl is optionally substituted with one or more substituents independently selected from halogen and $C_{1-4}$alkyl;

n is an integer from 0 to 1;

L is selected from the group consisting of

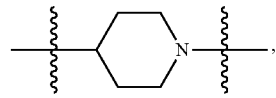

—$CH_2CH_2$—$NR^A$— and —$CH_2CH_2CH_2$—$NR^A$—; wherein $R^A$ is selected from the group consisting of hydrogen, methyl and ethyl; (and wherein the L substituent group is incorporated into the compound of formula (I) as drawn; more particularly, the L substituent group is incorporated into the compound of formula (I) such that the N atom of the L substituent group is bound to the C(O) of the compound of formula (I))

Y is selected from the group consisting of N and CH;

X is selected from the group consisting of $N(R^B)$, O and S; wherein $R^B$ is selected from the group consisting of hydrogen and $C_{1-4}$alkyl;

$R^2$ is selected from the group consisting of hydrogen, halogen, nitro, —$CO_2H$, —C(O)—$NR^CR^D$, -Q, —O-Q and —C(O)—NH-Q;

wherein $R^C$ and $R^D$ are each independently selected from the group consisting of hydrogen and $C_{1-4}$alkyl; alternatively, $R^C$ and $R^D$ are taken together with the nitrogen atom to which they are bound to form a ring structure selected from the group consisting of piperidin-1-yl, piperazin-1-yl, pyrrolidin-1-yl, morpholin-4-yl, 1,2,3,4-tetrahydroquinolin-1-yl and 1,2,3,4-tetrahydro-isoquinolin-2-yl;

wherein Q is selected from the group consisting of aryl, aralkyl, heterocyclyl, benzo[d][1,3]dioxolyl and 2,3-dihydro-benzo[b][1,4]dioxinyl;

wherein the aryl or heterocyclyl, whether alone or as part of a substituent group, is optionally substituted with one or more substituents independently selected from the group consisting of halogen, cyano, $C_{1-4}$alkyl, halogenated $C_{1-4}$alkyl, $C_{1-4}$alkoxy, halogenated $C_{1-4}$alkoxy, —$CO_2H$, —C(O)—$NR^ER^F$, —$SO_2$—$NR^ER^F$ and phenyl; wherein $R^E$ and $R^F$ are each independently selected from the group consisting of hydrogen and $C_{1-4}$alkyl;

and wherein the heterocyclyl contains one or more S heteroatoms, said heterocyclyl may be further optionally substituted on said one or more S heteroatoms with one to two oxo groups;

and pharmaceutically acceptable salts thereof.

The present invention is further directed to compounds of formula (II)

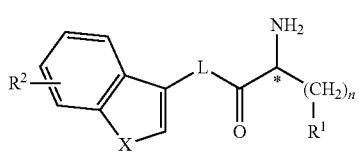

wherein

R¹ is selected from the group consisting of $C_{1-4}$alkyl, —C(O)—NH₂, $C_{3-6}$cycloalkyl, phenyl and 5 to 6 membered heteroaryl; wherein the heteroaryl is optionally substituted with one or more substituents independently selected from halogen and $C_{1-4}$alkyl;

n is an integer from 0 to 1;

L is selected from the group consisting of —CH₂CH₂—NR$^A$— and —CH₂CH₂CH₂—NR$^A$—; wherein R$^A$ is selected from the group consisting of hydrogen, methyl and ethyl; (and wherein the L substituent group is incorporated into the compound of formula (I) as drawn; more particularly, the L substituent group is incorporated into the compound of formula (I) such that the N atom of the L substituent group is bound to the C(O) of the compound of formula (I))

X is selected from the group consisting of N(R$^B$), O and S; wherein R$^B$ is selected from the group consisting of hydrogen and $C_{1-4}$alkyl;

R² is selected from the group consisting of hydrogen, halogen, nitro, —CO₂H, —C(O)—NR$^C$R$^D$, -Q, —O-Q and —C(O)—NH-Q;

wherein R$^C$ and R$^D$ are each independently selected from the group consisting of hydrogen and $C_{1-4}$alkyl; alternatively, R$^C$ and R$^D$ are taken together with the nitrogen atom to which they are bound to form a ring structure selected from the group consisting of piperidin-1-yl, piperazin-1-yl, pyrrolidin-1-yl, morpholin-4-yl, 1,2,3,4-tetrahydroquinolin-1-yl and 1,2,3,4-tetrahydro-isoquinolin-2-yl;

wherein Q is selected from the group consisting of aryl, aralkyl, heterocyclyl, benzo[d][1,3]dioxolyl and 2,3-dihydro-benzo[b][1,4]dioxinyl;

wherein the aryl or heterocyclyl, whether alone or as part of a substituent group, is optionally substituted with one or more substituents independently selected from the group consisting of halogen, cyano, $C_{1-4}$alkyl, halogenated $C_{1-4}$alkyl, $C_{1-4}$alkoxy, halogenated $C_{1-4}$alkoxy, —CO₂H, —C(O)—NR$^E$R$^F$, —SO₂—NR$^E$R$^F$ and phenyl; wherein R$^E$ and R$^F$ are each independently selected from the group consisting of hydrogen and $C_{1-4}$alkyl;

and wherein the heterocyclyl contains one or more S heteroatoms, said heterocyclyl may be further optionally substituted on said one or more S heteroatoms with one to two oxo groups;

and pharmaceutically acceptable salts thereof.

The present invention is further directed to processes for the preparation of the compounds of formula (I) and/or the compounds of formula (II). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by DPP-1 (cathepsin C) (e.g., a disorder selected from the group consisting of rheumatoid arthritis, asthma, chronic obstructive pulmonary disease, sepsis, irritable bowel disease, cystic fibrosis, and abdominal aortic aneurism) in a subject in need thereof comprising administering to the subject a therapeutically effective amount of any of the compounds or pharmaceutical compositions described above.

Another example of the invention is the use of any of the compounds described herein in the preparation of a medicament for treating: (a) rheumatoid arthritis, (b) asthma, (c) chronic obstructive pulmonary disease, (d) sepsis, (e) irritable bowel disease, (f) cystic fibrosis, or (g) abdominal aortic aneurism, in a subject in need thereof.

In another example, the present invention is directed to a compound as described herein for use in a methods for treating a disorder selected from the group consisting of rheumatoid arthritis, asthma, chronic obstructive pulmonary disease, sepsis, irritable bowel disease, cystic fibrosis, and abdominal aortic aneurism, in a subject in need thereof.

DETAILED DESCRIPTION OF THE INVENTION

The present invention is directed to compounds of formula (I)

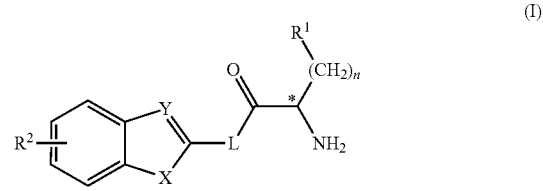

wherein R¹, R², X, Y, L and n are as herein defined, and pharmaceutically acceptable salts thereof. The present invention is further directed to compounds of formula (II)

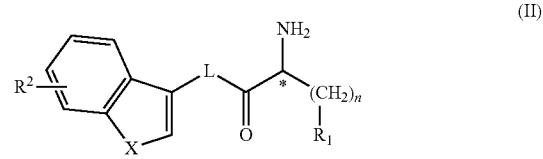

wherein R¹, R², X, Y, L and n are as herein defined, and pharmaceutically acceptable salts thereof. The compounds of formula (I) and formula (II) of the present invention are inhibitors of DPP-1, useful in the treatment of disorders, diseases and conditions mediated by DPP-1 (cathepsin C), including, but not limited to, rheumatoid arthritis, asthma, chronic obstructive pulmonary disease, sepsis, irritable bowel disease, cystic fibrosis, and abdominal aortic aneurism.

One skilled in the art will recognize that some of the variables (e.g. R¹, R², X, L and n, etc.) appear in compounds of formula (I) and compounds of formula (II). One skilled in the art will further recognize that wherein a particular substituent is selected for a given variable for a compound of formula (I), said selection is not intended to limit the scope of said variable for compounds of formula (II). Similarly, the selection of a particular substituent for a given variable for a compound of formula (II), is not intended to limit the scope of said variable for compounds of formula (I).

In an embodiment of the present invention, $R^1$ is selected from the group consisting of $C_{1-4}$alkyl, —C(O)—NH$_2$, $C_{3-6}$cycloalkyl and 5 to 6 membered heteroaryl; wherein the 5 to 6 membered heteroaryl is optionally substituted with one to two substituent selected from the group consisting of halogen and $C_{1-4}$alkyl. In another embodiment of the present invention, $R^1$ is selected from the group consisting of $C_{1-4}$alkyl, —C(O)—NH$_2$, $C_{4-6}$cycloalkyl and 5 to 6 membered heteroaryl; wherein the 5 to 6 membered heteroaryl is optionally substituted with a substituent selected from the group consisting of halogen and $C_{1-4}$alkyl.

In another embodiment of the present invention, $R^1$ is selected from the group consisting of ethyl, cyclobutyl, thien-2-yl, thien-3-yl, 2-bromo-thien-2-yl, 5-chloro-thien-2-yl, thiazol-2-yl, 4-methyl-thiazol-2-yl, pyrazol-1-yl, fur-2-yl, 1-methyl-imidazol-4-yl and amino-carbonyl. In another embodiment of the present invention, $R^1$ is selected from the group consisting of ethyl, thien-2-yl, thiazol-2-yl, fur-2-yl and 1-methyl-imidazol-4-yl. In another embodiment of the present invention, $R^1$ is selected from the group consisting of ethyl, thien-2-yl, thiazol-2-yl and fur-2-yl. In another embodiment of the present invention, $R^1$ is selected from the group consisting of ethyl, thien-2-yl and thiazol-2-yl. In another embodiment of the present invention, $R^1$ is thien-2-yl.

In another embodiment of the present invention, $R^1$ is $C_{1-4}$alkyl. In another embodiment of the present invention, $R^1$ is $C_{1-2}$alkyl. In another embodiment of the present invention, $R^1$ is ethyl.

In an embodiment of the present invention n is 0. In another embodiment of the present invention, n is 1.

In an embodiment of the present invention, L is

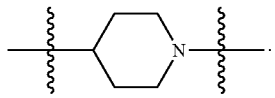

In another embodiment of the present invention, L is selected from the group consisting of —CH$_2$CH$_2$—N(R$^A$)— and —CH$_2$CH$_2$CH$_2$—N(R$^A$)—; wherein R$^A$ is selected from the group consisting of hydrogen, methyl and ethyl. In another embodiment of the present invention, L is —CH$_2$CH$_2$CH$_2$—N(R$^A$)—; wherein R$^A$ is selected from the group consisting of hydrogen, methyl and ethyl. In another embodiment of the present invention, L is —CH$_2$CH$_2$—NR$^A$—. In another embodiment of the present invention, L is —CH$_2$CH$_2$CH$_2$—NR$^A$—. In another embodiment of the present invention, L is —CH$_2$CH$_2$CH$_2$—NH—.

In another embodiment of the present invention, L is selected from the group consisting of

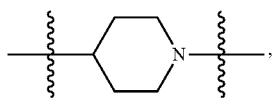

—CH$_2$CH$_2$—N(R$^A$)— and —CH$_2$CH$_2$CH$_2$—N(R$^A$)—; wherein R$^A$ is selected from the group consisting of hydrogen, methyl and ethyl. In another embodiment of the present invention, L is selected from the group consisting of

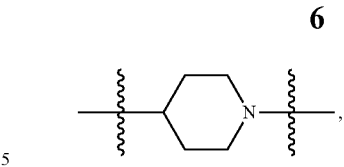

—CH$_2$CH$_2$—NH—, —CH$_2$CH$_2$CH$_2$—NH—, —CH$_2$CH$_2$CH$_2$—N(CH$_3$)— and —CH$_2$CH$_2$CH$_2$—N(CH$_2$CH$_3$)—. In another embodiment of the present invention, L is selected from the group consisting of

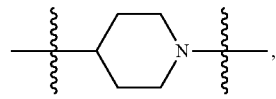 [SMILES: *C1CCN(*)CC1]

—CH$_2$CH$_2$—NH—, —CH$_2$CH$_2$CH$_2$—NH— and —CH$_2$CH$_2$CH$_2$—N(CH$_2$CH$_3$)—. In another embodiment of the present invention, L is selected from the group consisting of

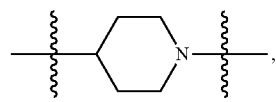

—CH$_2$CH$_2$CH$_2$—NH— and —CH$_2$CH$_2$CH$_2$—N(CH$_2$CH$_3$)—. In another embodiment of the present invention, L is selected from the group consisting of

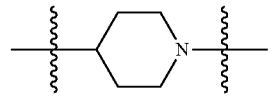 [SMILES: *C1CCN(*)CC1]

and —CH$_2$CH$_2$CH$_2$—NH—.

In an embodiment of the present invention, R$^A$ is selected from the group consisting of hydrogen, methyl and ethyl. In another embodiment of the present invention, R$^A$ is hydrogen.

In an embodiment of the present invention

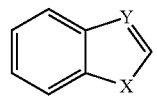

is selected from the group consisting of indolyl, 1-methyl-indolyl, benzofuryl, benzothienyl and benzimidazolyl.

In an embodiment of the present invention, Y is selected from the group consisting of N and CH; and X is selected from the group consisting of N(R$^B$), O and S; provided that when X is O or S, then Y is CH.

In an embodiment of the present invention Y is N. In another embodiment of the present invention, Y is CH. In an embodiment of the present invention X is O. In another embodiment of the present invention, X is S. In another embodiment of the present invention, X is NR$^B$. In another embodiment of the present invention, R$^B$ is selected from the group consisting of hydrogen, methyl, ethyl, isopropyl and t-butyl. In another embodiment of the present invention, R$^B$ is selected from the group consisting of hydrogen, methyl and ethyl. In another embodiment of the present invention, R$^B$ is selected from the group consisting of hydrogen and methyl. In another embodiment of the present invention, $R^B$ is hydrogen.

In an embodiment of the present invention, Y is selected from the group consisting of N and CH; and X is selected from the group consisting of $N(R^B)$, O and S; wherein $R^B$ is selected from the group consisting of hydrogen and $C_{1-2}$alkyl. In another embodiment of the present invention, Y is selected from the group consisting of CH and N; and X is selected from the group consisting of NH, $N(CH_3)$ and O; provided that when X is O, then Y is CH. In another embodiment of the present invention, Y is selected from the group consisting of CH and N; and X is selected from the group consisting of NH and O; provided that when X is O, then Y is CH. In another embodiment of the present invention, Y is CH; and X is NH.

In an embodiment of the present invention

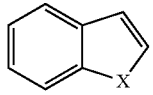

is selected from the group consisting of indolyl and benzothienyl. In another embodiment of the present invention, X is selected from the group consisting of $N(R^B)$ and S; wherein $R^B$ is selected from the group consisting of hydrogen and $C_{1-2}$alkyl. In another embodiment of the present invention, X is selected from the group consisting of S and NH.

In an embodiment of the present invention, $R^2$ is selected from the group consisting of hydrogen, halogen, nitro, —$CO_2H$, —$C(O)$—$NR^CR^D$, phenyl, —O-phenyl, heterocyclyl, and —$C(O)$—NH-Q; wherein $R^C$ and $R^D$ are each independently selected from the group consisting of hydrogen and $C_{1-4}$alkyl; alternatively, $R^C$ and $R^D$ are taken together with the nitrogen atom to which they are bound to form a ring structure selected from the group consisting of piperidin-1-yl, pyrrolidin-1-yl, 1,2,3,4-tetrahydroquinolin-1-yl and 1,2,3,4-tetrahydro-isoquinolin-2-yl;

wherein Q is selected from the group consisting of aryl, aralkyl, heterocyclyl, benzo[d][1,3]dioxolyl and 2,3-dihydro-benzo[b][1,4]dioxinyl; wherein the aryl or heterocyclyl, whether alone or as part of a substituent group, is optionally substituted with one to two substituents independently selected from the group consisting of halogen, cyano, $C_{1-4}$alkyl, fluorinated $C_{1-4}$alkyl, $C_{1-4}$alkoxy, fluorinated $C_{1-4}$alkoxy, —$CO_2H$, —$C(O)NR^ER^F$, —$SO_2$—$NR^ER^F$ and phenyl; wherein $R^E$ and $R^F$ are each independently selected from the group consisting of hydrogen and $C_{1-2}$alkyl; and wherein the heterocyclyl contains one or more S heteroatoms, said heterocyclyl may be further optionally substituted on said one or more S heteroatoms with one to two oxo groups.

In another embodiment of the present invention, $R^2$ is selected from the group consisting of hydrogen, halogen, nitro, carboxy, phenyl, —O-phenyl, —$C(O)$—$NR^CR^D$ and —$C(O)$—NH-Q; wherein $R^C$ and $R^D$ are each independently selected from the group consisting of hydrogen and $C_{1-2}$alkyl; alternatively, $R^C$ and $R^D$ are taken together with the nitrogen atom to which they are bound to form a ring structure selected from the group consisting of 1,2,3,4-tetrahydroquinolin-1-yl and 1,2,3,4-tetrahydro-isoquinolin-2-yl;

wherein Q is selected from the group consisting of phenyl, naphthyl, —$C_{1-2}$alkyl-phenyl, heterocyclyl, benzo[d][1,3]dioxolyl and 2,3-dihydro-benzo[b][1,4]dioxinyl; wherein the phenyl or heterocyclyl, whether alone or as part of a substituent group, is optionally substituted with one to two substituents independently selected from the group consisting of halogen, cyano, $C_{1-4}$alkyl, fluorinated $C_{1-2}$alkyl, $C_{1-4}$alkoxy, fluorinated $C_{1-2}$alkoxy, —$CO_2H$, —$C(O)NH_2$, —$SO_2$—$NH_2$ and phenyl; and wherein the heterocyclyl contains one or more S heteroatoms, said heterocyclyl may be further optionally substituted on said one or more S heteroatoms with one to two oxo groups.

In another embodiment of the present invention, $R^2$ is selected from the group consisting of hydrogen, 5-bromo, 5-(carboxy), 5-(nitro), 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(2-(aminocarbonyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 6-(diethylamino-carbonyl), 5-(phenyl-amino-carbonyl), 5-(3-chlorophenyl-amino-carbonyl), 5-(4-chlorophenyl-amino-carbonyl), 5-(2-fluorophenyl-amino-carbonyl), 5-(3-fluorophenyl-amino-carbonyl), 5-(4-fluorophenyl-amino-carbonyl), 5-(3-methylphenyl-amino-carbonyl), 5-(4-methylphenyl-amino-carbonyl), 5-(2-isopropylphenyl-amino-carbonyl), 5-(4-isopropylphenyl-amino-carbonyl), 5-(4-t-butylphenyl-amino-carbonyl), 5-(2-methoxyphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4-dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(3,5-dimethoxyphenyl-amino-carbonyl), 5-(naphth-1-yl-amino-carbonyl), 5-(benzyl-amino-carbonyl), 5-([1,2,4]triazol-3-yl-amino-carbonyl), 5-(pyrid-3-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(benzimidazol-4-yl-amino-carbonyl), 5-(benzimidazol-5-yl-amino-carbonyl), 5-(1-methyl-benzimidazol-4-yl-amino-carbonyl), 5-(pyrazol-3-yl-amino-carbonyl), 5-(5-phenyl-pyrazol-3-yl-amino-carbonyl), 5-(1H-pyrazolo[3,4-d]pyrimidin-4-yl-amino-carbonyl), 5-(1,1-dioxo-benzothiophen-6-yl-amino-carbonyl), 5-(1,2,3,4-tetrahydro-quinolin-1-yl-amino-carbonyl), 5-(1,2,3,4-tetrahydro-quinolin-1-yl-carbonyl), 5-(1,2,3,4-tetrahydro-isoquinolin-2-yl-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl).

In another embodiment of the present invention, $R^2$ is selected from the group consisting of hydrogen, 5-bromo, 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(2-(aminocarbonyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 5-(phenyl-amino-carbonyl), 5-(3-chlorophenyl-amino-carbonyl), 5-(4-chlorophenyl-amino-carbonyl), 5-(2-fluorophenyl-amino-carbonyl), 5-(3-fluorophenyl-amino-carbonyl), 5-(4-fluorophenyl-amino-carbonyl), 5-(3-methylphenyl-amino-carbonyl), 5-(4-methylphenyl-amino-carbonyl), 5-(2-isopropylphenyl-amino-carbonyl), 5-(4-isopropylphenyl-amino-carbonyl), 5-(4-t-butylphenyl-amino-carbonyl), 5-(2-methoxyphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4-dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(3,5-dimethoxyphenyl-amino-carbonyl), 5-(naphth-1-yl-amino-carbonyl), 5-(pyrid-3-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(benzimidazol-4-yl-amino-carbonyl), 5-(benzimidazol-5-yl-amino-carbonyl), 5-(1-methyl-benzimidazol-4-yl-amino-carbonyl), 5-(pyrazol-3-yl-amino-carbonyl), 5-(5-phenyl-pyrazol-3-yl-amino-carbonyl), 5-(1H-pyrazolo[3,4-d]pyrimidin-4-yl-amino-carbonyl), 5-(1,1-dioxo-benzothiophen-6-yl-amino-carbonyl), 5-(1,2,3,4-tetrahydro-quinolin-1-yl-amino-carbonyl), 5-(1,2,3,4-tetrahydro-quinolin-1-yl-carbonyl), 5-(1,2,3,4-tetrahydro-isoquinolin-2-yl-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl).

In another embodiment of the present invention, $R^2$ is selected from the group consisting of 5-bromo, 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 5-(3-chlorophenyl-amino-carbonyl), 5-(4-chlorophenyl-amino-carbonyl), 5-(3-fluorophenyl-amino-carbonyl), 5-(3-methylphenyl-amino-carbonyl), 5-(4-isopropylphenyl-amino-carbonyl), 5-(4-t-butylphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4-dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(naphth-1-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl).

In another embodiment of the present invention, $R^2$ is selected from the group consisting of 5-(4-methoxy-phenyl), 5-(3,4-dimethoxy-phenyl), 5-(3,5-dimethoxy-phenyl), 5-(3-cyano-phenyl), 5-(4-carboxy-phenyl), 5-(3-(aminocarbonyl)-phenyl), 5-(phenoxy), 5-(3,4-dimethoxy-phenoxy), 5-(3-methoxyphenyl-amino-carbonyl), 5-(4-methoxyphenyl-amino-carbonyl), 5-(2,6-dimethylphenyl-amino-carbonyl), 5-(3,4-dimethoxyphenyl-amino-carbonyl), 5-(quinolin-3-yl-amino-carbonyl), 5-(quinolin-5-yl-amino-carbonyl), 5-(quinolin-6-yl-amino-carbonyl), 5-(isoquinolin-5-yl-amino-carbonyl), 5-(isoquinolin-8-yl-amino-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl).

In another embodiment of the present invention, $R^2$ is selected from the group consisting of 5-(3,4-dimethoxyphenyl) and 5-(3,4-dimethoxyphenyl-amino-carbonyl). In another embodiment of the present invention, $R^2$ is hydrogen.

In an embodiment of the present invention, the $R^2$ group is bound at the 5- or 6-position of the

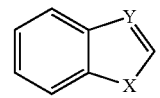

core. In another embodiment, the $R^2$ group is bound at the 5-position of the

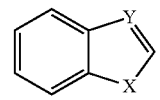

core. In an embodiment of the present invention, the $R^2$ group is bound at the 5- or 6-position of the

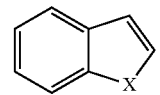

core. In another embodiment, the $R^2$ group is bound at the 5-position of the

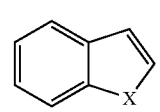

core.

In an embodiment, the present invention is directed to compounds of formula (I) wherein the stereo-center denoted with the "*" symbol is present in (R) configuration. Preferably, the compound of formula (I) is present in the (R) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

In an embodiment, the present invention is directed to compounds of formula (I) wherein the stereo-center denoted with the "*" symbol is present in (S) configuration. Preferably, the compound of formula (I) is present in the (S) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

In an embodiment, the present invention is directed to compounds of formula (II) wherein the stereo-center denoted with the "*" symbol is present in (R) configuration. Preferably, the compound of formula (II) is present in the (R) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

In an embodiment, the present invention is directed to compounds of formula (II) wherein the stereo-center denoted with the "*" symbol is present in (S) configuration. Preferably, the compound of formula (II) is present in the (S) configurations in an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

Additional embodiments of the present invention, include those wherein the substituents selected for one or more of the variables defined herein (i.e.

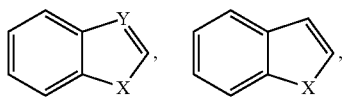

$R^1$, $R^2$, L, X, Y and n) are independently selected to be any individual substituent or any subset of substituents selected from the complete list as defined herein. In another embodiment of the present invention is any single compound or subset of compounds selected from the representative compounds listed in Tables 1 to 4 below.

Representative compounds of formula (I) of the present invention are as listed in Tables 1 to 3 below. One skilled in the art will recognize that in the recitation of the bonding position of the $R^2$ substituent group to the

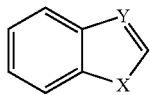

core of the compounds of formula (I) (including in Tables 1 to 3 below), the position of the $R^2$ substituent group shall be denoted according to the following numbering scheme:

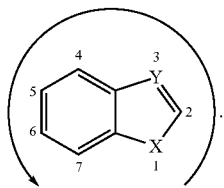

One skilled in the art will further recognize that in Tables 1 to 3 which follow herein, in the column headed "$R^2$", the recitation of #-(substituted group) shall denote the position at which the $R^2$ group is bound to the

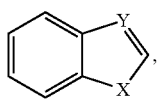

followed by the identification of the substituent group within the parentheses. For example, the notation 5-(3,4-dimethoxy-phenyl) shall denoted a 3,4-dimethoxy-phenyl group bound at the 5-position of the

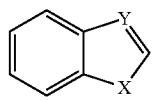

core.

TABLE 1

Representative Compounds of Formula (I)

| ID No. | $R^2$ | core | * | n | $R^1$ |
|---|---|---|---|---|---|
| 1 | hydrogen | benzofuran | S | 1 | thien-2-yl |
| 2 | 5-(3,4-dimethoxy-phenyl) | indole | S | 1 | thien-2-yl |
| 3 | 5-(2,3-dihydro-benzo[b][1,4]dioxin-6-yl) | indole | S | 1 | thien-2-yl |
| 4 | 5-(4-methoxy-phenyl) | indole | S | 1 | thien-2-yl |
| 5 | 5-(3-(amino-carbonyl)-phenyl) | indole | S | 1 | thien-2-yl |
| 6 | 5-(benzo[d][1,3]dioxol-5-yl) | indole | S | 1 | thien-2-yl |
| 7 | 5-((3,4-dimethoxy-phenyl)-amino-carbonyl) | indole | S | 1 | thien-2-yl |
| 8 | 5-(3-(amino-carbonyl)-phenyl) | indole | S | 1 | thiazol-2-yl |
| 9 | 5-(3,4-dimethoxy-phenyl) | indole | S | 0 | ethyl |

TABLE 1-continued

Representative Compounds of Formula (I)

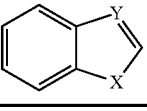

| ID No. | R² | X/Y ring | * | n | R¹ |
|---|---|---|---|---|---|
| 10 | 5-(3,4-dimethoxy-phenyl) | 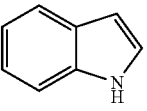 | S | 1 | 5-bromo-thien-2-yl |
| 11 | 5-(3,4-dimethoxy-phenyl) | 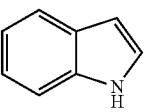 | S | 1 | pyrazol-1-yl |
| 12 | 5-(3,4-dimethoxy-phenyl) | 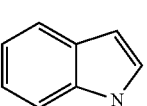 | S | 1 | cyclobutyl |
| 13 | 5-(3,4-dimethoxy-phenyl) | 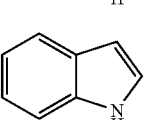 | S | 1 | fur-2-yl |
| 14 | 5-(3,4-dimethoxy-phenyl) | 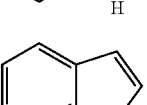 | S | 1 | 1-methyl-imidazol-4-yl |
| 15 | 5-(3,4-dimethoxy-phenyl) | 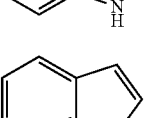 | S | 1 | thien-3-yl |
| 16 | 5-bromo | 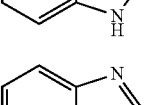 | S | 1 | thien-2-yl |
| 17 | 5-((3,4-dimethoxy-phenyl)-amino-carbonyl) | 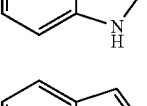 | S | 1 | thien-2-yl |
| 18 | 5-(3,4-dimethoxy-phenyl) | 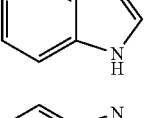 | S | 1 | thien-2-yl |
| 19 | 5-(3-(amino-carbonyl)-phenyl) | 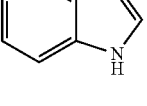 | S | 1 | thien-2-yl |
| 20 | 5-(3-cyano-phenyl) | 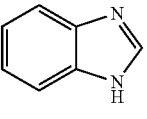 | S | 1 | thien-2-yl |
| 21 | 5-(3-carboxyl-phenyl) | 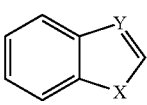 | S | 1 | thien-2-yl |
| 22 | 5-(3,4-dimethoxy-phenyl) | 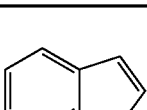 | S | 1 | 4-methyl-thiazol-2-yl |
| 23 | 5-(pyrid-3-yl) | 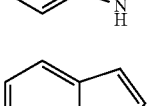 | S | 1 | thien-2-yl |
| 24 | 5-(3,4-dimethoxy-phenyl) | 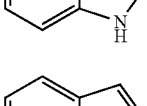 | S | 1 | 5-chloro-thien-2-yl |
| 25 | 5-(6-methoxy-pyrid-3-yl) | 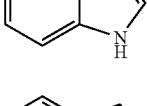 | S | 1 | thien-2-yl |
| 26 | 5-(pyrid-4-yl) | 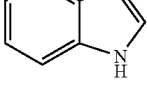 | S | 1 | thien-2-yl |
| 27 | 5-(4-carboxy-phenyl) | 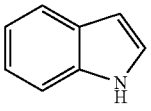 | S | 1 | thien-2-yl |
| 28 | 5-(3,4-dimethoxy-phenyl) | 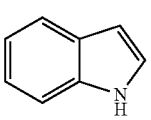 | R/S | 0 | thien-2-yl |
| 29 | 5-(3,4-dimethoxy-phenyl) | 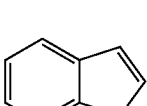 | R/S | 0 | fur-2-yl |
| 30 | 5-(3,4-dimethoxy-phenyl) | 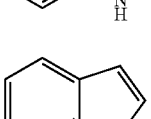 | R/S | 0 | thien-3-yl |

TABLE 2

Representative Compounds of Formula (I)

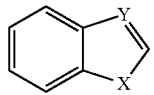

| ID No. | R² | [ring] | * | n | R¹ |
|---|---|---|---|---|---|
| 35 | hydrogen | 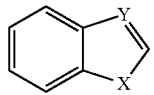 | S | 1 | thien-2-yl |
| 36 | 5-(3,4-dimethoxy-phenyl-amino-carbonyl) | 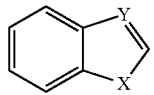 | S | 0 | ethyl |
| 37 | hydrogen | 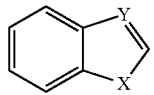 | S | 1 | thien-2-yl |
| 38 | hydrogen | 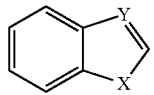 | S | 0 | ethyl |
| 39 | hydrogen | 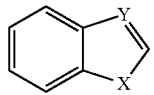 | S | 0 | ethyl |

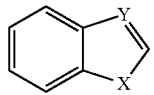

| 40 | hydrogen | 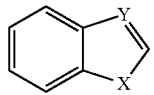 | S | 0 | ethyl |
|---|---|---|---|---|---|
| 41 | hydrogen | 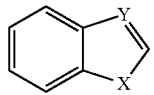 | S | 0 | ethyl |
| 42 | hydrogen | 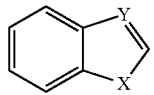 | S | 0 | ethyl |
| 45 | 5-(phenyl) | 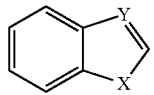 | S | 0 | ethyl |
| 46 | 6-(diethylamino-carbonyl) | 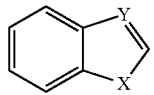 | S | 0 | ethyl |
| 47 | 5-(carboxy) | 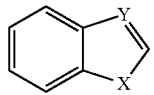 | S | 0 | ethyl |
| 48 | 5-([1,2,4]triazol-3-yl-amino-carbonyl) | 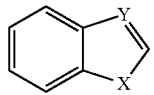 | S | 0 | ethyl |
| 49 | 5-(nitro) | 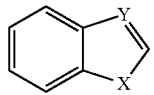 | S | 0 | ethyl |
| 50 | 5-(3,4-dimethoxy-phenyl-amino-carbonyl) | 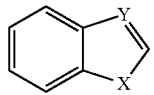 | S | 0 | ethyl |
| 51 | 5-(phenyl-amino-carbonyl) | 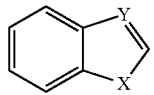 | S | 0 | ethyl |
| 52 | 5-(pyrid-3-yl-amino-carbonyl) | 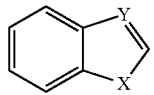 | S | 0 | ethyl |
| 53 | 5-(benzyl-amino-carbonyl) | 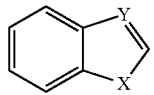 | S | 0 | ethyl |
| 54 | 5-(naphth-1-yl-amino-carbonyl) | 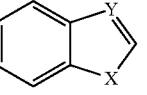 | S | 0 | ethyl |
| 55 | 5-(quinolin-5-yl-amino-carbonyl) | 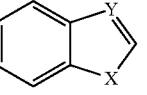 | S | 0 | ethyl |
| 56 | hydrogen | 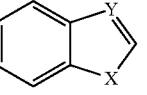 | S | 1 | thien-2-yl |
| 57 | 5-(benzothiazol-6-yl-amino-carbonyl) | 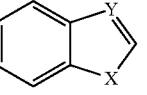 | S | 0 | ethyl |

TABLE 2-continued

Representative Compounds of Formula (I)

| ID No. | R² | (structure) | * | n | R¹ |
|---|---|---|---|---|---|
| 58 | 5-(3,4-dimethoxy-phenyl-amino-carbonyl) | 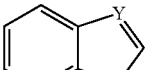 | S | 0 | ethyl |
| 59 | 5-(1-methyl-benzimidazol-4-yl-amino-carbonyl) | 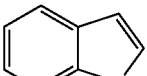 | S | 0 | ethyl |
| 61 | 5-(pyrazol-3-yl-amino-carbonyl) | 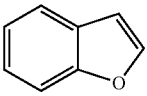 | S | 0 | ethyl |
| 62 | 5-(5-phenyl-pyrazol-3-yl-amino-carbonyl) | 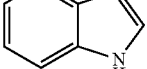 | S | 0 | ethyl |
| 63 | 5-(1H-pyrazolo[3,4-d]pyrimidin-4-yl-amino-carbonyl) | 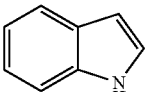 | S | 0 | ethyl |
| 64 | 5-(quinolin-3-yl-amino-carbonyl) | 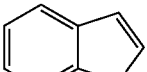 | S | 0 | ethyl |
| 65 | 5-(isoquinolin-5-yl-amino-carbonyl) | 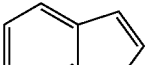 | S | 0 | ethyl |
| 66 | 5-(quinolin-8-yl-amino-carbonyl | 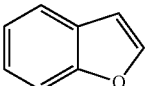 | S | 0 | ethyl |
| 67 | 5-(quinolin-6-yl-amino-carbonyl) | 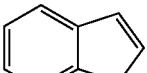 | S | 0 | ethyl |
| 68 | 5-(isoquinolin-8-yl-amino-carbonyl) | 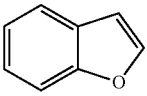 | S | 0 | ethyl |
| 69 | 5-(2,3-dihydro-benzo[b][1,4]dioxin-6-yl) | 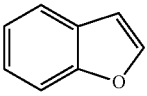 | S | 0 | ethyl |
| 70 | 5-(benzo[d][1,3]dioxol-5-yl) | 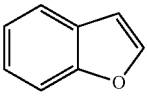 | S | 0 | ethyl |
| 71 | 5-(1,2,3,4-tetrahydro-quinolin-1-yl-carbonyl) | 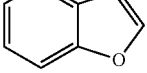 | S | 0 | ethyl |
| 72 | 5-(benzimidazol-5-yl-amino-carbonyl) | 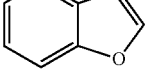 | S | 0 | ethyl |
| 73 | 5-(1,2,3,4-tetrahydro-quinolin-4-yl-amino-carbonyl) | 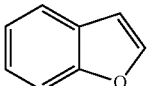 | S | 0 | ethyl |
| 74 | 5-(carboxy) | 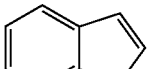 | S | 0 | ethyl |
| 75 | 5-(4-methyl-phenyl-amino-carbonyl) | 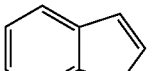 | S | 0 | ethyl |
| 76 | 5-(4-chloro-phenyl-amino-carbonyl) | 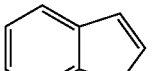 | S | 0 | ethyl |
| 77 | 5-(4-methoxy-phenyl-amino-carbonyl) | 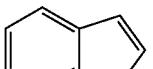 | S | 0 | ethyl |
| 78 | 5-(4-t-butyl-phenyl-amino-carbonyl) | 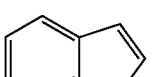 | S | 0 | ethyl |
| 79 | 5-(4-fluoro-phenyl-amino-carbonyl) | 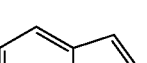 | S | 0 | ethyl |
| 80 | 5-(4-isopropyl-phenyl-amino-carbonyl) | 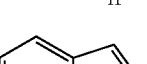 | S | 0 | ethyl |
| 81 | 5-(3,4-difluoro-phenyl-amino-carbonyl) | 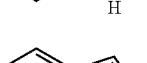 | S | 0 | ethyl |
| 82 | 5-(3,4-dichloro-phenyl-amino-carbonyl) | 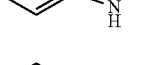 | S | 0 | ethyl |
| 83 | 5-(3,4-dimethyl-phenyl-amino-carbonyl) | 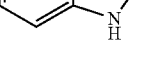 | S | 0 | ethyl |

TABLE 2-continued

Representative Compounds of Formula (I)

| ID No. | R² | | * | n | R¹ |
|---|---|---|---|---|---|
| 84 | 5-(1,2,3,4-tetrahydro-isoquinolin-2-yl-carbonyl) | 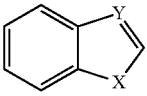 | S | 0 | ethyl |
| 85 | 5-(benzimidazol-4-yl-amino-carbonyl) | 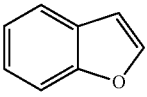 | S | 0 | ethyl |
| 86 | 5-(1,1-dioxo-benzothiophen-6-yl-amino-carbonyl) | 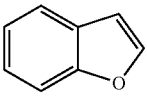 | S | 0 | ethyl |
| 87 | 5-(2-fluorophenyl-amino-carbonyl) | 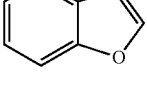 | S | 0 | ethyl |
| 88 | 5-(2-methoxy-phenyl-amino-carbonyl) | 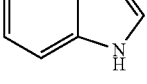 | S | 0 | ethyl |
| 89 | 5-(2-isopropyl-phenyl-amino-carbonyl) | 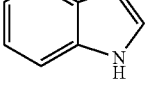 | S | 0 | ethyl |
| 90 | 5-(3-fluorophenyl-amino-carbonyl) | 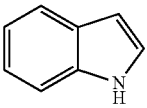 | S | 0 | ethyl |
| 91 | 5-(3-chlorophenyl-amino-carbonyl) | 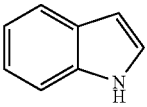 | S | 0 | ethyl |
| 92 | 5-(3-methoxyphenyl-amino-carbonyl) | 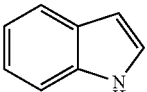 | S | 0 | ethyl |
| 93 | 5-(3-methylphenyl-amino-carbonyl) | 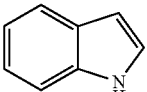 | S | 0 | ethyl |
| 94 | 5-(3,5-dimethoxy-phenyl-amino-carbonyl) | 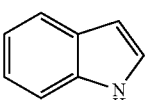 | S | 0 | ethyl |
| 95 | 5-(2,6-dimethyl-phenyl-amino-carbonyl) | 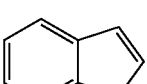 | S | 0 | ethyl |
| 96 | 5-(3,5-dimethoxy-phenyl) | 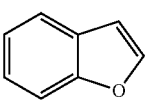 | S | 0 | ethyl |
| 97 | 5-(3,4-dimethoxy-phenyl-amino-carbonyl) | 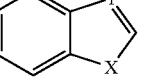 | S | 1 | thien-2yl |
| 98 | 5-(phenyl-oxy) | 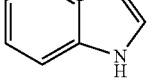 | S | 0 | ethyl |
| 99 | 5-(3,4-dimethoxy-phenyl-oxy) | 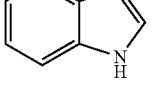 | S | 0 | ethyl |
| 100 | 5-(phenyl) | 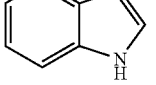 | S | 0 | ethyl |
| 101 | 5-(4-fluorophenyl) | 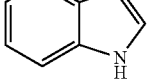 | S | 0 | ethyl |
| 102 | 5-(4-trifluoromethyl-phenyl) | 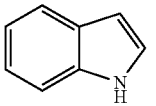 | S | 0 | ethyl |
| 103 | 5-(3-(amino-carbonyl)-phenyl) | 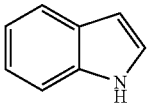 | S | 0 | ethyl |
| 104 | 5-(4-methoxy-phenyl) | 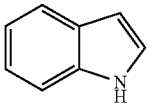 | S | 0 | ethyl |
| 105 | 5-(4-trifluoro-methoxy-phenyl) | 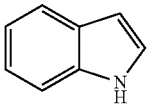 | S | 0 | ethyl |
| 106 | 5-(3,4-dimethoxy-phenyl-amino-carbonyl) | 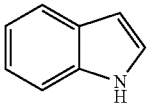 | S | 1 | thien-2yl |
| 108 | 5-(3,4-dimethoxy-phenyl-amino-carbonyl) | 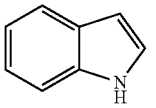 | S | 0 | ethyl |

TABLE 2-continued

Representative Compounds of Formula (I)

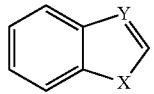

| ID No. | R² | [benzo-fused ring] | * | n | R¹ |
|---|---|---|---|---|---|
| 109 | 5-(3,5-di(trifluoromethyl)-phenyl) | indole | S | 0 | ethyl |
| 110 | 5-(3,4-dimethoxy-phenyl-amino-carbonyl) | indole | S | 0 | ethyl |
| 111 | 5-(4-(amino-carbonyl)-phenyl) | indole | S | 0 | ethyl |
| 112 | 5-(benzo[d][1,3]dioxol-5-yl) | indole | S | 0 | ethyl |
| 113 | 5-(3-(aminosulfonyl)-phenyl) | indole | S | 0 | ethyl |
| 114 | 5-(pyrid-4-yl) | indole | S | 0 | ethyl |
| 115 | 5-(3,4-dimethoxy-phenyl-amino-carbonyl) | indole | S | 1 | amino-carbonyl- |
| 116 | 5-(2-(amino-carbonyl)-phenyl) | indole | S | 0 | ethyl |
| 117 | 5-(3,4-dimethoxy-phenyl-amino-carbonyl) | indole | S | 1 | thien-2-yl |

TABLE 3

Representative Compounds of Formula (I)

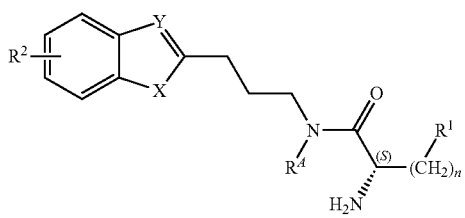

| ID No. | R² | [benzo-fused ring] | R⁴ | n | R¹ |
|---|---|---|---|---|---|
| 107 | 5-(3,4-dimethoxy-phenyl-amino-carbonyl) | indole | methyl | 0 | ethyl |
| 118 | 5-(3,4-dimethoxy-phenyl-amino-carbonyl) | indole | ethyl | 1 | thien-2-yl |

Representative compounds of formula (II) of the present invention are as listed in Table 4, below.

TABLE 4

Representative Compounds of Formula (II)

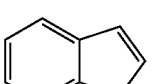

| ID No. | R² | [benzo-fused ring] | * | n | R¹ |
|---|---|---|---|---|---|
| 43 | hydrogen | benzothiophene | S | 0 | ethyl |
| 44 | hydrogen | indole | S | 0 | ethyl |

In another embodiment, the present invention is directed to compounds of formula (I) whose $IC_{50}$, measured according to the procedure described in Biological Example 1, is less than or equal to about 10 μM, preferably less than or equal to about 5.0 μM, more preferably less than or equal to about 1.0 μM, more preferably less than or equal to about 0.5 μM, more preferably less than or equal to about 0.1 μM.

In another embodiment, the present invention is directed to compounds of formula (II) whose $IC_{50}$, measured according to the procedure described in Biological Example 1, is less than or equal to about 10 μM, preferably less than or equal to about 5.0 μM, preferably less than or equal to about 1.0 μM, more preferably less than or equal to about 0.5 μM, more preferably less than or equal to about 0.1 μM.

As used herein, "halogen" shall mean chlorine, bromine, fluorine and iodine.

As used herein, the term "alkyl" whether used alone or as part of a substituent group, shall include straight and branched carbon chain compositions of one to six carbon atoms. For example, alkyl radicals include methyl, ethyl, propyl, isopropyl, butyl, isobutyl, sec-butyl, t-butyl, n-pentyl, and the like. The prefix "$C_{X-Y}$" wherein X and Y are integers, when used with alkyl shall mean a carbon chain composition of between X and Y carbon atoms. For example, the term "$C_{1-4}$alkyl" shall mean a straight or branched carbon chain composition of 1 to 4 carbon atoms.

One skilled in the art will recognize that the terms "-(alkyl)-" and "—($C_{1-4}$alkyl)-" shall denote any alkyl or $C_{1-4}$alkyl carbon chain as herein defined, wherein said alkyl or $C_{1-4}$alkyl chain is divalent and is further bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CCl_3$, —$CH_2$—$CF_3$, —$CH_2CCl_3$, —$CF_2$—$CF_2$—$CF_2$—$CF_3$, and the like. Similarly, as used herein, unless otherwise noted, the term "fluorinated $C_{1-4}$alkyl" shall mean any $C_{1-4}$alkyl group as defined above substituted with at least one fluoro atom. Suitable examples include but are not limited to —$CF_3$, —$CH_2$—$CF_3$, —$CF_2$—$CF_2$—$CF_2$—$CF_3$, and the like. Preferably, the halogenated or fluorinated alkyl is —$CF_3$.

As used herein, the term "alkoxy" whether used alone or as part of a substituent group, shall denote an oxygen ether radical of any of the above described straight and branched carbon chain compositions of one to six carbon atoms. For example, alkoxy radicals include methoxy, ethoxy, propoxy, isopropoxy, n-butoxy, isobutoxy, sec-butoxy, t-butoxy, n-pentoxy, and the like. The prefix "$C_{X-Y}$" wherein X and Y are integers, when used with alkoxy shall mean an oxygen radical of any of the above described carbon chain composition of between X and Y carbon atoms. For example, the term "$C_{1-4}$alkoxy" shall mean an oxygen ether radical of any straight or branched carbon chain composition of 1 to 4 carbon atoms. Suitably examples include methoxy, ethoxy, propoxy, isopropoxy, n-butoxy, isobutoxy, sec-butoxy and t-butoxy.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCF_3$, —$OCCl_3$, —$OCH_2$—$CF_3$, —$OCH_2CCl_3$, —$OCF_2$—$CF_2$—$CF_2$—$CF_3$, and the like. Similarly, as used herein, unless otherwise noted, the term "fluorinated $C_{1-4}$alkoxy" shall mean any $C_{1-4}$alkoxy group as defined above substituted with at least one fluoro atom. Suitable examples include but are not limited to —$OCF_3$, —$OCH_2$—$CF_3$, —$OCF_2$—$CF_2$—$CF_2$—$CF_3$, and the like. Preferably, the halogenated or fluorinated alkoxy is —$OCF_3$.

As used herein, unless otherwise noted, "aryl" shall refer to unsubstituted carbocylic aromatic groups such as phenyl, naphthyl, and the like. As used herein, unless otherwise noted, "aralkyl" shall mean any $C_{1-4}$alkyl group substituted with an aryl group such as phenyl, naphthyl and the like. For example, benzyl, phenylethyl-, phenyl-n-propyl-, naphth-1-ylmethyl-, and the like.

As used herein, unless otherwise noted, the term "$C_{3-6}$cycloalkyl" shall mean any stable 3-6 membered monocyclic, saturated ring system, for example cyclopropyl, cyclobutyl, cyclopentyl and cyclohexyl.

As used herein, unless otherwise noted, "5 to 6 membered heteroaryl" shall denote any five or six membered monocyclic aromatic ring structure containing at least one heteroatom selected from the group consisting of O, N and S, optionally containing one to three additional heteroatoms independently selected from the group consisting of O, N and S. The heteroaryl group may be attached at any heteroatom or carbon atom of the ring such that the result is a stable structure. Examples of suitable heteroaryl groups include, but are not limited to, furyl, thienyl, pyrrolyl, oxazolyl, thiazolyl, pyrazolyl, imidazolyl, isoxazolyl, isothiazolyl, triazolyl, thiadiazolyl, pyridyl, pyridazinyl, pyrimidinyl, pyrazinyl, pyranyl, and the like. Preferred heteroaryl groups include, but are not limited to, thienyl, thiazolyl, pyrazolyl, imidazolyl, pyridyl and triazolyl.

As used herein, the term "heterocyclyl" shall denote any five to seven membered monocyclic, saturated, partially unsaturated or aromatic ring structure containing at least one heteroatom selected from the group consisting of O, N and S, optionally containing one to three additional heteroatoms independently selected from the group consisting of O, N and S; or any nine to ten membered saturated, partially unsaturated, partially aromatic (including benzo-fused) or aromatic bicyclic ring system containing at least one heteroatom selected from the group consisting of O, N and S, optionally containing one to four additional heteroatoms independently selected from the group consisting of O, N and S. The heterocyclyl group may be attached at any heteroatom or carbon atom of the ring such that the result is a stable structure. Examples of suitable heterocyclyl groups include, but are not limited to, thienyl, thiazolyl, pyrazolyl, imidazolyl, pyridyl, triazolyl, quinolinyl, isoquinolinyl, benzothiazolyl, benzimidazolyl, benzothiophenyl, 1H-pyrazolo[3,4-d]pyrimidinyl, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 1,2,3,4-tetrahydro-quinolinyl, 1,2,3,4-tetrahydro-isoquinolinyl, and the like. Preferred heterocyclyl groups include, but are not limited to, thienyl, thiazolyl, pyrazolyl, imidazolyl, pyridyl, triazolyl, quinolinyl, isoquinolinyl, benzothiazolyl, benzimidazolyl, benzothiophenyl, piperidinyl, piperazinyl, morpholinyl, pyrrolidinyl, 1H-pyrazolo[3,4-d]pyrimidinyl, 1,2,3,4-tetrahydro-quinolinyl and 1,2,3,4-tetrahydro-isoquinolinyl.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

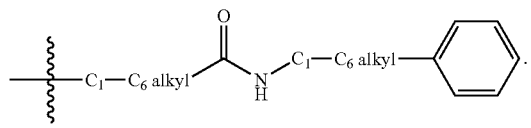

Abbreviations used in the specification, particularly the Schemes and Examples, are as follows:

| | |
|---|---|
| Boc or BOC = | tert-Butoxycarbonyl |
| BOP-Cl = | Benzotriazol-1-yloxy-tris(dimethylamino)phosphoniium hexafluorophosphate chloride |
| Cbz or CBz = | Benzyloxy-carbonyl- |
| COPD = | Chronic Obstructive Pulmonary Disease |
| DCM = | Dichloromethane |
| DIPEA or DIEA = | Diisopropylethylamine |
| DMAP = | 4-N,N-Dimethylaminopyridine |
| DMF = | N,N-Dimethylformamide |
| DMSO = | Dimethylsulfoxide |
| DPP-1 = | Dipeptidyl Peptidase-1 (Cathepsin C) |
| DTT = | Dithiothreitol |
| EDC or EDCI = | 1-ethyl-3-(3-dimethylaminopropyl) carbodiimide |
| EtOAc = | Ethyl Acetate |
| GR-AMC = | Glycine-Arginine-amino-4-methyl-coumain |
| GSH = | Glutathione |
| HATU = | O-(7-Azabenzotriazol-1-yl)-N,N,N'',N''-Tetramethyl Uronium Hexafluorophosphate |
| HBTU = | O-(1H-Benzotriazol-1-yl)-N,N,N',N'-tetramethyluronium hexafluorophosphate |
| HEPES = | 4-(2-Hydroxyethyl)-1-Piperizine Ethane Sulfonic Acid |
| HOBT or HOBt = | 1-Hydroxybenzotriazole |
| HPLC = | High Pressure Liquid Chromatography |
| MeCN = | Acetonitrile |
| MeOH = | Methanol |
| MOM = | Methoxymethyl |
| MTBE = | Methyl tert-butyl ether |
| NMP = | N-methyl-2-pyrrolidinone |
| Pd(OAc)$_2$Cl$_2$ = | Palladium acetate dichloride |
| Pd/C = | Palladium on Carbon (catalyst) |
| Pd(dppf)Cl$_2$ = | Dichloro[1,1'-bis(diphenylphosphine)ferrocene]palladium(II) |
| Pd(dppp)Cl$_2$ = | Bis(diphenylphosphino)propane palladium (II) chloride |
| Pd(PhCN)$_2$Cl$_2$ = | Dichlorobis(benzonitrile)palladium (II) |
| Pd(PPh$_3$)$_4$ = | Tetrakistriphenylphosphine palladium (0) |
| Pd(PPh$_3$)$_2$Cl$_2$ = | Bis(triphenylphosphine)palladium (II) chloride |
| PPh$_3$ = | Triphenylphosphine |
| P(o-tolyl)$_3$ = | Tri-o-tolylphosphine |
| TEA = | Triethylamine |
| TFA = | Trifluoroacetic Acid |
| THF = | Tetrahydrofuran |
| THP = | Tetrahydropyranyl |
| TMS = | Trimethylsilyl |

As used herein, unless otherwise noted, the term "isolated form" shall mean that the compound is present in a form which is separate from any solid mixture with another compound(s), solvent system or biological environment. In an embodiment, the compound of formula (I) is prepared as an isolated form. In another embodiment, the compound of formula (II) is prepared as an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the compound of formula (I) is present as a substantially pure compound. In another embodiment, the compound of formula (II) is present as a substantially pure compound.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the compound of formula (I) is present in a form which is substantially free of corresponding salt form(s). In another embodiment, the compound of formula (II) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "DPP-1 mediated disorder" shall include any condition, disease or disorder which may be mediated through inhibition of DPP-1 activity. One skilled in the art will recognize that disorders mediated by DPP-1 include, but are not limited to (a) disorders of the respiratory tract: including obstructive diseases of the airways including asthma, including bronchial, allergic, intrinsic, extrinsic, exercise-induced, drug induce (including aspirin and NSAID-induced) and dust induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sacroidosis; farmer's lung and related diseases; hypersensitive pnemonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vascullitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

(b) skin disorders: psoriasis, atopic dermatitis, contact dermatatis or other eczematous deramtoses, and delayed-type hypersensitivity reactions; phyto- and photodermatitis; seborrhoeic dermatistis, dermatitis herptiformis, lichen planus, lichen slerosus et atrophica, pyoderma gangrenosum, skin sarcoid, discoid lupus erythematosus, pemphigus, pemphigoid, epidermolysis bullosa, urticaria, angioderma, vasculitides, toxic erythams, cutaceous eosinopiliass, alopecia greata, male-pattern baldness, Sweet's syndrome, Weber-Christian syndrome, erythema multiforma; cellulitis, both infective and non-infective; panniculitis; cutaceous lymphomas, non-melanoma skin cancer and other dysplastic lesions; drug-induced disorders including fixed-drug eruptions;

(c) eye disorders: blepharitis, conjunctivitis, including perennial and vernal allergic conjunctivitis; iritis; anterior and posterior uveitis; choroiditis; autoimmune, degenerative or inflammatory disorders affecting the retina; opthalmitis including sympathetic opthalmitis; sarcoidosis; infections including viral, fugal and bacterial;

(d) genitourinary disorders: nephritis including interstitial and glomerulnephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction;

(e) allograft rejection disorders: acute and chronic following, for example, transplantation of kidney, heart, liver, lung, bone marrow, skin or cornea or following blood transfusion; or chronic graft versus host disease;

(f) auto-immune and allergic disorders including rheumatoid arthritis, irritable bowel syndrome, systemic lupus erythematosus, multiple sclerosis, Hashimoto's thyroiditis, Grave's disease, Addison's disease, diabetes mellitus, idiopathic thrombocytopaenic purpura, eosinophilic fasciitis, hyper-IgE syndrome, antiphospholipid syndrome and Sazary syndrome;

(g) cancers: including treatment of common cancers including prostate, breast, lung, ovarian, pancreatic, bowel and colon, stomach, skin and brain tumors and malignancies affecting the bone marrow (including leukaemias) and lymphoproliferative systems, such as Hodgkin's and non-Hodgkin's lymphoma; including the prevention and treatment of metastatic disease and tumor recurrences, and paraneoplstic syndrome; and (h) infectious diseases: viral diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoser virus (VZV), rhinovirus, adenovirus, coronavirus, influenza, para-influenza; bacterial diseases such as tubercuavium, leprosy; other infectious diseases such as fungal diseases, Chlamydia, candida, aspergillus, cryptococcal meningitis, pneumocystis carnii, cryptosporidiosis, histoplasmosis, toxoplasmosis, trypanosome infection and leishmaniasis.

In another embodiment, the present invention is directed to methods for the treatment and/or prevention of a DDP-1 mediated disorder; wherein the DPP-1 mediated disorder is selected from the group consisting of chronic obstructive pulmonary disease (COPD), asthma, acute lung injury, adult respiratory distress syndrome, abdominal or thoracic aneurism, rheumatoid arthritis, osteoarthritis, multiple sclerosis, sepsis and taxoplasmosis.

In another embodiment, the present invention is directed to methods for the treatment and/or prevention of a DDP-1 mediated disorder; wherein the DPP-1 mediated disorder is selected from the group consisting of rheumatoid arthritis, asthma, chronic obstructive pulmonary disease (COPD), sepsis, irritable bowel disease, cystic fibrosis, and abdominal aortic aneurism.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee = ([\alpha\text{-}obs]/[\alpha\text{-max}]) \times 100.$$

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

Compounds of formula (I) wherein L is

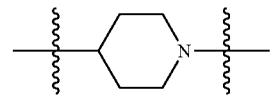

may be prepared according to the process outlined in Scheme 1.

Scheme 1

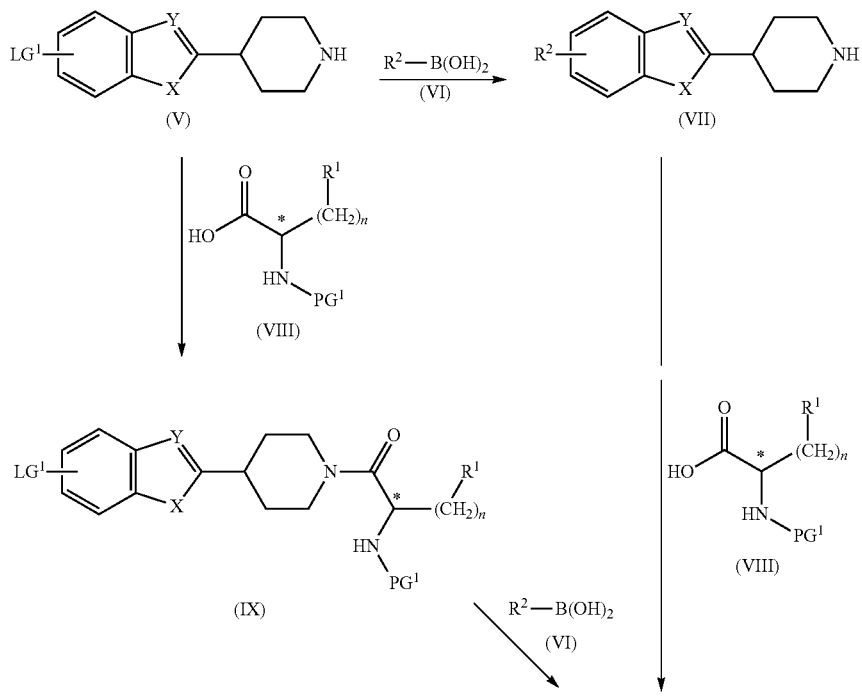

-continued

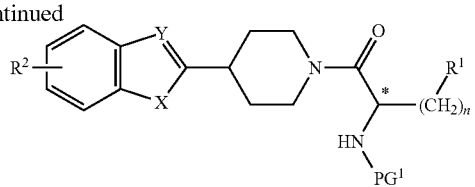

(X)

↓

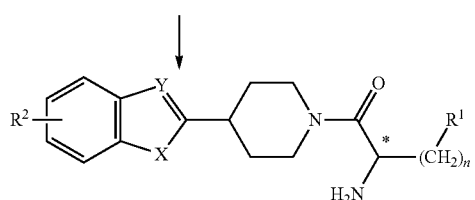

(Ia)

Accordingly, a suitably substituted compound of formula (V), wherein $LG^1$ is a suitably selected leaving group such as bromo, chloro, iodo, and the like, preferably bromo, a known compound or compound prepared by known methods, is reacted with a suitably substituted boronic acid, a compound of formula (VI), a known compound or compound prepared by known methods, in the presence of a suitably selected catalysts such as $Pd(PPh_3)_2Cl_2$, $Pd(OAc)_2Cl_2$, $Pd(dppf)Cl_2$, $Pd(dppp)Cl_2$, and the like; in the presence of a suitably selected base such as $Na_2CO_3$, $K_2CO_3$, $Cs_2CO_3$, and the like; in a suitably selected aprotic solvent such as 1,4-dioxane, DMF, toluene, and the like; to yield the corresponding compound of formula (VII).

The compound of formula (VII) is reacted with a suitably substituted compound of formula (VIII), wherein $PG^1$ is a suitably selected nitrogen protecting group such as BOC, CBz, and the like, a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (X).

Alternatively, a suitably substituted compound of formula (V) wherein $LG^1$ is a suitably selected leaving group such as bromo, chloro, iodo, and the like, preferably bromo, a known compound or compound prepared by known methods, is reacted with a suitably substituted compound of formula (VIII), wherein $PG^1$ is a suitably selected nitrogen protecting group such as BOC, CBz, and the like, a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (IX).

The compound of formula (IX) is reacted with a suitably substituted boronic acid, a compound of formula (VI), a known compound or compound prepared by known methods, in the presence of a suitably selected catalysts such as $Pd(PPh_3)_2Cl_2$, $Pd(OAc)_2Cl_2$, $Pd(dppf)Cl_2$, $Pd(dppp)Cl_2$, and the like; in the presence of a suitably selected base such as $Na_2CO_3$, $K_2CO_3$, $Cs_2CO_3$, and the like; in a suitably selected aprotic solvent such as 1,4-dioxane, DMF, toluene, and the like; to yield the corresponding compound of formula (X).

The compound of formula (X) is de-protected according to known methods, to yield the corresponding compound of formula (Ia). For example, wherein $PG^1$ is BOC, the compound of formula (X) may be de-protected by reacting with a suitably selected acid such as HCl, TFA, and the like; in a suitably selected solvent such DCM, diethyl ether, and the like.

One skilled in the art will recognize that wherein the compound of formula (Ia) X is $N(R^B)$, said compound may be similarly prepared as described above or alternatively be prepared as the corresponding compound wherein X is NH and then further reacted with a suitably selected alkylating agent, according to known methods.

Compounds of formula (I) wherein L is —$(CH_2)_{2-3}$—NH— may be prepared according to the process outlined in Scheme 2 below.

Scheme 2

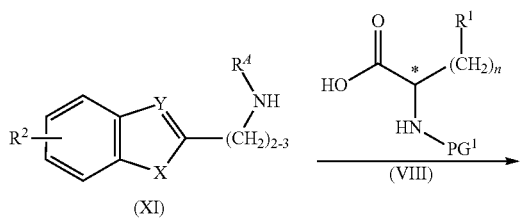

(XI)     (VIII)

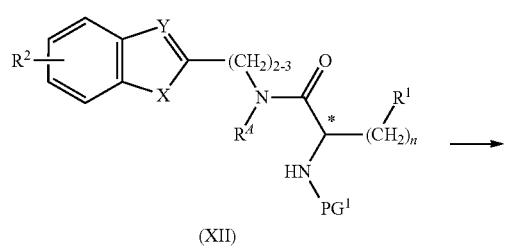

(XII)

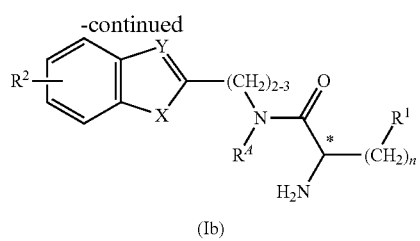

(Ib)

Accordingly, a suitably substituted compound of formula (XI), a known compound or compound prepared by known methods, is reacted with a suitably substituted compound of formula (VIII), wherein $PG^1$ is a suitably selected nitrogen protecting group such as BOC, CBz, and the like, a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (XII).

The compound of formula (XII) is de-protected according to known methods, to yield the corresponding compound of formula (Ib). For example, wherein $PG^1$ is BOC, the compound of formula (XII) may be de-protected by reacting with a suitably selected acid such as HCl, TFA, and the like; in a suitably selected solvent such DCM, diethyl ether, and the like.

Compounds of formula (I) wherein Y is CH, X is N($R^B$) and L is —$(CH_2)_{2-3}$—NH— may be prepared according to the process outlined in Scheme 3, below.

Scheme 3

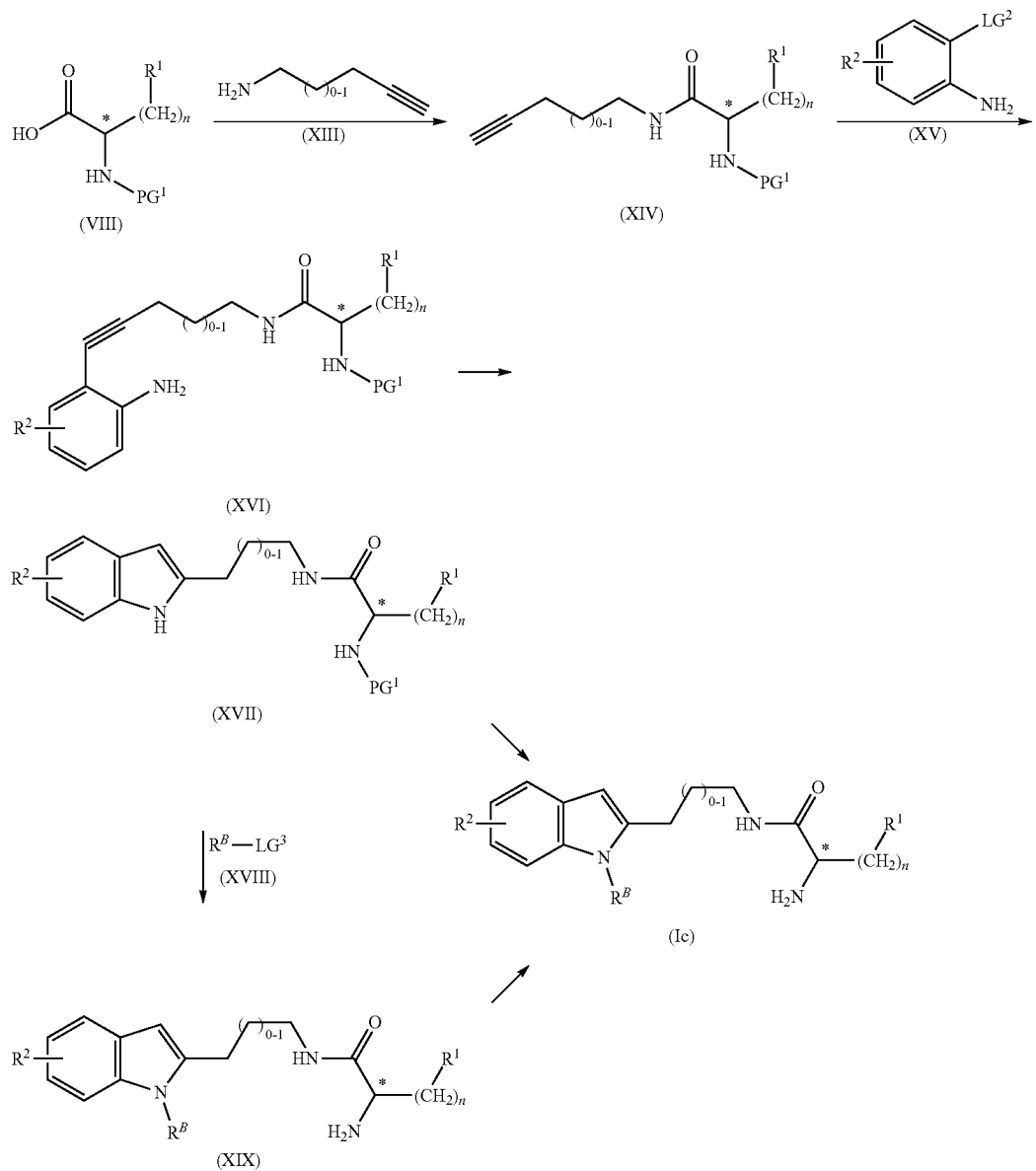

Accordingly, a suitably substituted compound of formula (VIII), wherein PG1 is a suitably selected nitrogen protecting group such as Boc, Cbz, trifluoroacetyl, and the like, a known compound or compound prepared by known methods, is reacted with a compound of formula (XIII), a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (XIV).

The compound of formula (XIV) is reacted with a suitably substituted compound of formula (XV), wherein $LG^2$ is a suitably selected leaving group such as iodo, bromo, chloro, and the like, a known compound or compound prepared by known methods, in the presence of a suitably selected palladium catalysts such as $Pd(PPh_3)_4$, $PdCl_2(PPh_3)_2$, $Pd(PhCN)_2Cl_2$, and the like; in the presence of CuI; in a suitably selected solvent such as diethylamine, DMF, and the like; to yield the corresponding compound of formula (XVI).

The compound of formula (XVI) is reacted under ring closure conditions, more particularly in the presence of a suitably selected catalyst such as $Pd(PhCN)_2Cl_2$, $Pd(PPh_3)_4$, $PdCl_2(PPh_3)_2$, and the like; in a suitably selected solvent such as DMF, diethylamine, and the like; to yield the corresponding compound of formula (XVII).

The compound of formula (XVII) is optionally reacted with a suitably selected alkylating agent, a compound of the formula (XVIII); in the presence of a suitably selected base such as NaH, and the like; in a suitably selected solvent such as DMF, THF, diethyl ether, and the like; to yield the corresponding compound of formula (XIX).

The compound of formula (XVII) or the compound of formula (XIX) is de-protected to remove the $PG^1$ group according to known methods, to yield the corresponding compound of formula (Ic). For example, wherein $PG^1$ is —C(O)—$CF_3$, the compound of formula (XVII) or compound of formula (XVIII) is reacted with a suitably selected base such as NaOH, KOH, and the like; in a suitably selected solvent such as THF, methanol, and the like; to yield the corresponding compound of formula (Ic).

One skilled in the art will recognize that compounds of formula (I) wherein $R^2$ is —C(O)—$NR^CR^D$ or —C(O)—NH-Q may be prepared from the corresponding compound of formula (I) wherein $R^2$ is —C(O)OH by reacting with a suitably substituted amine (a compound of formula $NHR^CR^D$ or $NH_2$-Q), a known compound or compound prepared by known methods, in the presence of a coupling agent such as BOP-Cl, HATU, and the like; in the presence of a suitably selected base such as TEA, DIPEA, and the like; in a suitably selected organic solvent such as DCM, acetonitrile, THF, and the like.

One skilled in the art will further recognize that compounds of formula (I) wherein Y is CH, X is $N(R^B)$ and L is —$(CH_2)_{2-3}$—NH— and wherein $R^2$ is —O-Q, may similarly be prepared according to the process outlined in Scheme 3 above, by substituting a compound of formula (XXVI)

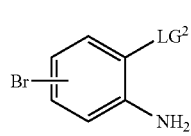

(XXVI)

for the compound of formula (XV) and reacting as described above, to yield the corresponding compound (XXVII)

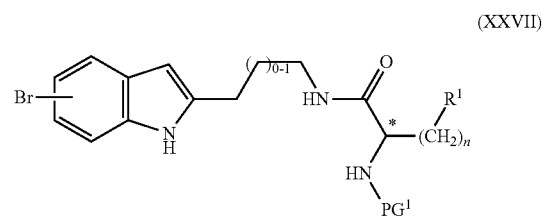

(XXVII)

which compound of formula (XXVII) is then reacted with a suitably substituted compound of formula Q-OH; in the presence of CuI; in the presence of a suitably selected base such as $Cs_2CO_3$, $K_2CO_3$, and the like; in a suitably selected solvent such as 1,4-dioxane, THF, and the like; to yield the corresponding compound of formula (XXVIII)

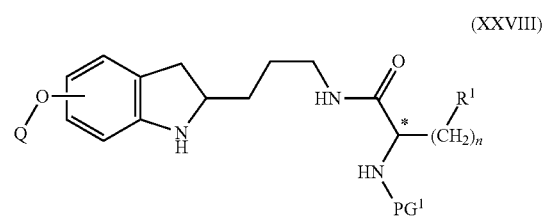

(XXVIII)

which compound of formula (XXVIII) is then de-protected according to known methods, to remove the $PG^1$ protecting group; to yield the desired compound of formula (I), wherein Y is CH, X is $N(R^B)$, L is —$(CH_2)_{2-3}$—NH— and wherein $R^2$ is —O-Q.

Compounds of formula (I) wherein Y is CH, X is $N(R^B)$ and L is —$CH_2CH_2CH_2$—NH— may be prepared according to the process outlined in Scheme 4, below.

Scheme 4

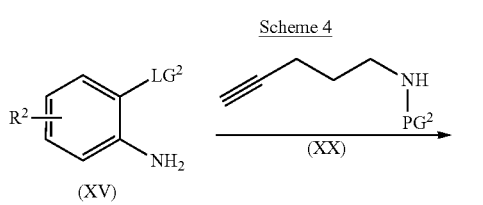

(XV) (XX)

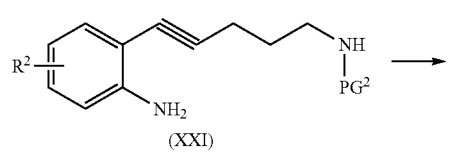

(XXI)

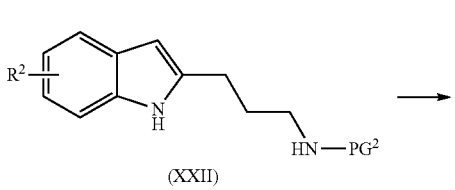

(XXII)

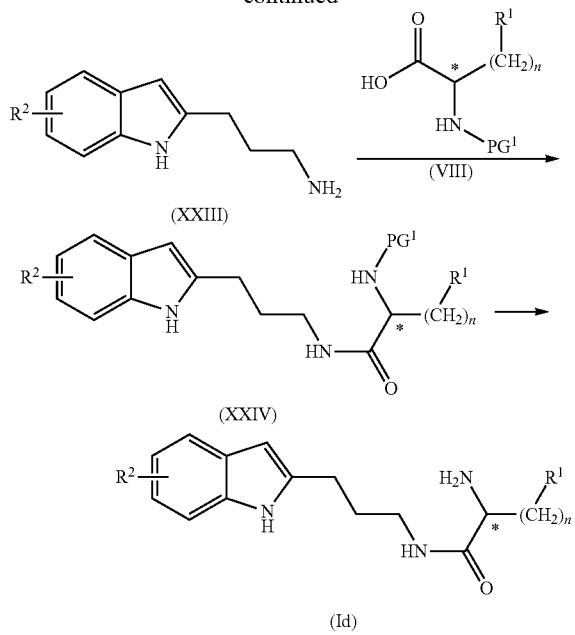

Accordingly, a suitably substituted compound of formula (XV), wherein LG2 is a suitably selected leaving group such as iodo, bromo, chloro, and the like, a known compound or compound prepared by known methods, is reacted with a compound of formula (XX), wherein $PG^2$ is a suitably selected nitrogen protecting group such as BOC, CBz, —C(O)CF$_3$, and the like, a known compound or compound prepared by known methods (for example by protecting the compound of formula (XIII), according to known methods); in the presence of a suitably selected palladium catalysts such as Pd(PPh$_3$)$_4$, PdCl$_2$(PPh$_3$)$_2$, Pd(PhCN)$_2$Cl$_2$, and the like; in the presence of CuI; in a suitably selected solvent such as diethylamine, DMF, and the like; to yield the corresponding compound of formula (XXI).

The compound of formula (XXI) is reacted under ring closure conditions, more particularly in the presence of a suitably selected catalyst such as Pd(PhCN)$_2$Cl$_2$, Pd(PPh$_3$)$_4$, PdCl$_2$(PPh$_3$)$_2$, and the like; in a suitably selected solvent such as DMF, diethylamine, and the like; to yield the corresponding compound of formula (XXII).

The compound of formula (XXII) is de-protected according to known methods, to yield the corresponding compound of formula (XXIII). For example, wherein $PG^2$ is BOC, the compound of formula (XXII) is de-protected by reacting with a suitably selected acid such as HCl, TFA, and the like, in a suitably selected organic solvent such as DCM, 1,4-dioxane, and the like.

The compound of formula (XXIII) is reacted with a suitably substituted compound of formula (VIII), wherein $PG^1$ is a suitably selected nitrogen protecting group such as BOC, CBz, —C(O)CF$_3$, and the like, a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (XXIV).

The compound of formula (XXIV) is de-protected according to known methods, to yield the corresponding compound of formula (Id). For example, wherein $PG^1$ is BOC, the compound of formula (XXIV) is de-protected by reacting with a suitably selected acid such as HCl, TFA, and the like, in a suitably selected organic solvent such as DCM, 1,4-dioxane, and the like.

One skilled in the art will recognize that for compounds of formula (I) wherein L is —CH$_2$CH$_2$CH$_2$—NH—, Y is CH, X is N(R$^B$) and wherein R$^B$ is other than hydrogen may be prepared by reacting the compound of formula (XXIV) with a suitably selected alkylating agent, as previously described, and the resulting product de-protected according to known methods.

Compounds of formula (I) wherein L is —(CH$_2$)$_{2-3}$—N(R$^A$)— and wherein R$^A$ is other than hydrogen may be similarly prepared according to the processes as outlined in the Schemes above, by selecting and substituting a suitably substituted compound of formula (XXV)

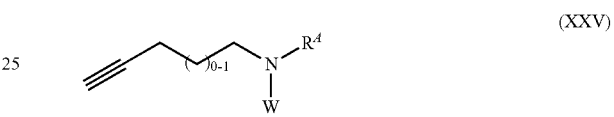

wherein W is hydrogen, a known compound or compound prepared by known methods, for the compound of formula (XIII) in Scheme 3, above; or by selecting and substituting a suitably substituted compound of formula (XXV), wherein W is a nitrogen protecting group such as BOC, CBz, —C(O)CF$_3$, and the like, a known compound or compound prepared by known methods, for the compound of formula (XX) in Scheme 4 above.

Compounds of formula (II) wherein L is —CH$_2$CH$_2$CH$_2$—N(R$^A$)— may be prepared according to the process outlined in Scheme 5, below.

Scheme 5

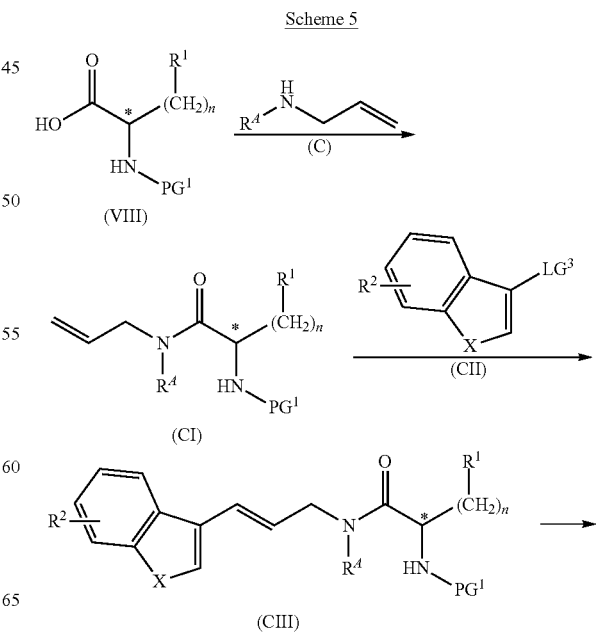

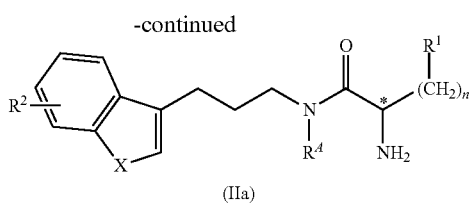

(IIa)

Accordingly, a suitably substituted compound of formula (VIII), wherein $PG^1$ is a suitably selected nitrogen protecting group such as BOC, CBz, —C(O)CF$_3$, and the like, a known compound or compound prepared by known methods, is reacted with a suitably substituted compound of formula (C), a known compound of compound prepared by known methods; in the presence of a suitably selected coupling agent such as HBTU, HATU, HOBt in combination with EDC, and the like; in the presence of a suitably selected organic base such as TEA, DIPEA, pyridine, and the like; optionally in the presence of a catalyst such as DMAP, and the like; in a suitably selected organic solvent such as DMF, DCM, NMP, and the like; to yield the corresponding compound of formula (CI).

The compound of formula (CI) is reacted with a suitably substituted compound of formula (CII), wherein $LG^3$ is a suitably selected leaving group such as bromo, chloro, iodo, and the like; in the presence of a suitably selected palladium catalyst such as Pd(OAc)$_2$, Pd(PPh$_3$)$_4$, PdCl$_2$(PPh$_3$)$_2$, and the like; in the presence of a suitably selected phosphorous agent such as P(o-tolyl)$_3$, PPh$_3$, and the like; in the presence of a suitably selected base such as TEA, DIPEA, pyridine, and the like; in a suitably selected organic solvent such as acetonitrile, DMF, toluene, and the like; to yield the corresponding compound of formula (CIII).

The compound of formula (CIII) is reacted with a source of hydrogen, such as hydrogen gas in the presence of a suitably selected catalyst such as Pd/C; in a suitably selected organic solvent such as methanol, ethanol, and the like, to yield the corresponding compound of formula (IIa).

One skilled in the art will recognize that compounds of formula (II) wherein L is —CH$_2$CH$_2$—N(R$^A$)— may be similarly prepared according to the process outlined in Scheme 5 above, by selecting and substituting a suitably substituted compound of formula (CIV)

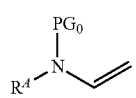

(CIV)

wherein $PG^0$ is a suitably selected nitrogen protecting groups, for the compound of formula (C); and reacting as described above, to yield the corresponding compound of formula (IIb)

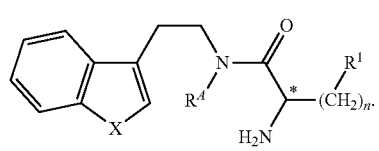

(IIb)

One skilled in the art will further recognize that compounds of formula (II) wherein X is N(R$^B$) may be similarly prepared as described in Scheme 5 above, by selecting and substituting a suitably substituted compound of formula (CV)

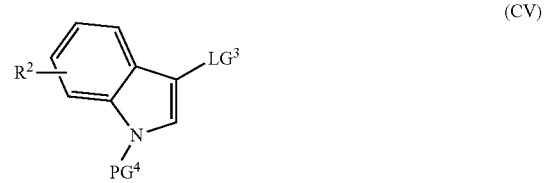

(CV)

wherein $PG^4$ is a suitably selected nitrogen protecting group such as BOC, CBz, —C(O)CF$_3$, and the like, for the compound of formula (CII), and reacted as described above, to yield the corresponding compound of formula (CVI)

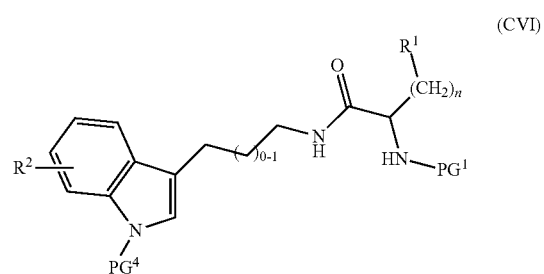

(CVI)

The compound of formula (CVI) is then de-protected sequentially or simultaneously, according to known methods, and then further optionally substituted by reacting with a suitably substituted alkylating agent, to yield the corresponding compound of formula (IIa).

The present invention further comprises pharmaceutical compositions containing one or more compounds of formula (I) and/or one or more compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular.

In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1,000 mg or any amount or range therein, and may be given at a dosage of from about 0.01 mg/kg/day to about 100 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1,000 mg of the compound, or any amount or range therein; preferably about 1.0 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by DPP-1 is required.

The daily dosage of the products may be varied over a wide range from 0.1 to about 10,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1,000 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.1 mg/kg to about 50.0 mg/kg of body weight per day, or any amount or range therein. More preferably, from about 0.1 mg/kg to about 25.0 mg/kg of body weight per day, or any amount or range therein. More preferably, from about 0.1 mg/kg to about 15.0 mg/kg of body weight per day, or any amount or range therein. More preferably, from about 0.1 mg/kg to about 10.0 mg/kg of body weight per day, or any amount or range therein. More preferably, from about 0.1 mg/kg to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. For example, Methot, N., et al., "In Vivo Inhibition of Serine Protease Processing Requires a High Fractional Inhibition of Cathepsin C", *Molecular Pharmacology*, (2008), Vol. 73, No. 6, pp 1857-1865 disclose an in vivo assay in rats for measuring inhibition of Cathepsin C (DPP-1).

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

(S)—N-(3-(1H-indol-2-yl)propyl)-2-aminobutanamide (Compound #40)

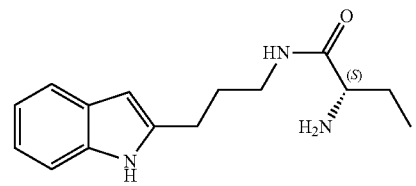

STEP A: Pent-4-yn-1-amine

A 1-L round bottom flask was charged with 2-(pent-4-ynyl)isoindoleine-1,2-dione (25.3 g, 0.119 mol), ethanol (390 mL) and water (4.4 mL). Hydrazine (7.8 mL, 0.248 mol) was added and the resulting mixture was stirred at room temperature for 24 h. Water (90 mL) was added and the resulting mixture acidified with 2N HCl to pH 3, then stirred at room temperature for 30 minutes. The resulting solid was filtered off and the filtrate was concentrated in vacuo. Water (90 mL) was added to the resulting residue and the mixture cooled using an ice/water bath. A 10 M NaOH solution (100 mL) was added slowly and the resulting mixture was stirred at room temperature for 15 minutes. The resulting mixture was then extracted with dichloromethane (2×600 mL), the organic layer was dried with sodium sulfate, filtered, and concentrated in vacuo to yield pent-4-yn-1-amine as an oil, which was used in the next step without further purification. $^1$H NMR (300 MHz, CDCl$_3$) δ 2.81 (t, J=6.8 Hz, 2H), 2.24-2.31 (m, 2H), 1.96 (s, 1H), and 1.62-1.71 (m, 2H).

STEP B: (S)—N-(pent-4-ynyl)-2-(2,2,2-trifluoroacetamido)butanamide

A 500 mL round bottom flask was charged with (S)-2-aminobutanoic acid (5.0 g, 0.048 mol) and dichloromethane (170 mL). The resulting mixture was cooled using an ice/water bath. Trifluoroacetic anhydride (8.8 mL, 0.063 mol) was added slowly and the resulting mixture stirred at room temperature for 18 h. The resulting mixture was then concentrated in vacuo to yield 2-(S)-(2,2,2-trifluoroacetylamino)-butyric acid as an oil which was used without further purification.

A 500 mL round bottom flask was charged with 2-(S)-(2,2,2-trifluoroacetylamino)-butyric acid (5.0 g, 0.025 mol), 1-hydroxybenzotriazole hydrate (4.5 g, 0.033 mol), N-(3-dimethylaminopropyl)-N'-ethylcarbodiimide hydrochloride (6.4 g, 0.033 mol), 4-(dimethylamino)pyridine (0.02 g, 0.163 mmol), and dimethylformamide (95 mL). To the resulting mixture was then added triethylamine (10.6 mL, 0.076 mol) and pent-4-yn-1-amine (2.7 g, 0.033 mol). The resulting mixture was stirred at room temperature for 22 h, then concentrated in vacuo to yield a residue which was purified via flash silica gel chromatography (Analogix IF-280, SF65-400 g column, gradient 90:10-40:60 Heptane:EtOAc) to yield (S)—N-(pent-4-ynyl)-2-(2,2,2-trifluoroacetamido)butanamide. $^1$H NMR (300 MHz, CDCl$_3$) δ4.46-4.53 (m, 1H), 3.32-3.48 (m, 2H), 2.23-2.29 (m, 2H), 2.00 (s, 1H), 1.86-1.98 (m, 2H), 1.71-1.83 (m, 2H), and 0.91-0.98 (m, 3H).

STEP C: N-[5-(2-aminophenyl)pent-4-ynyl]-2-(S)-(2,2,2-trifluoroacetylamino)butyramide A 50 mL round bottom flask was charged with (S)—N-(pent-4-ynyl)-2-(2,2,2-trifluoroacetamido)butanamide (110 mg, 0.42 mmol), 2-iodoaniline (89.0 mg, 0.41 mmol), copper iodide (13.0 mg, 0.068 mmol), palladium tetrakistriphenylphosphine (47 mg, 0.041 mmol), and diethylamine (12.6 mL). The resulting mixture was stirred at room temperature for 4 h, concentrated in vacuo and the resulting residue purified via flash silica gel chromatography (Analogix IF-280, SF25-40 g column, gradient 90:10-10:90 Heptane:EtOAc) to yield N-[5-(2-aminophenyl)pent-4-ynyl]-2-(S)-(2,2,2-trifluoroacetylamino)butyramide. $^1$H NMR (300 MHz, CDCl$_3$) δ 7.21-7.24 (m, 1H), 7.07-7.12 (m, 1H), 6.64-6.71 (m, 1H), 6.42-6.46 (m, 1H), 4.38-4.45 (m, 1H), 3.39-3.53 (m, 2H), 2.53 (t, J=6.8 Hz, 2H), 1.67-1.96 (m, 4H), and 0.88-0.93 (m, 3H).

STEP D: (S)—N-(3-(1H-indol-2-yl)propyl)-2-(2,2,2-trifluoroacetamido)butanamide

A 50 mL round bottom flask was charged with N-[5-(2-aminophenyl)pent-4-ynyl]-2-(S)-(2,2,2-trifluoroacetylamino)butyramide (130 mg, 0.37 mmol), dichlorobis(benzonitrile)palladium (II) (38.0 mg, 0.099 mmol), and dimethylformamide (4.1 mL) and the resulting mixture heated to 80° C. for 22 h. The resulting mixture was then concentrated in-vacuo and the resulting residue purified via flash silica gel chromatography (Analogix IF-280, SF25-40 g column, gradient 90:10-50:50 Heptane:EtOAc) to yield (S)—N-(3-(1H-indol-2-yl)propyl)-2-(2,2,2-trifluoroacetamido)butanamide. $^1$H NMR (300 MHz, CDCl$_3$) δ 7.48-7.53 (m, 1H), 7.32 (d, J=7.9 Hz, 1H), 7.04-7.15 (m, 2H), 6.23 (s, 1H), 4.32-4.39 (m, 1H), 3.31-3.38 (m, 2H), 2.71-2.75 (m, 2H), 1.82-1.95 (m, 3H), 1.63-1.77 (m, 1H), and 0.90-0.95 (m, 3H); MS (ES$^+$) 356 (M+1).

STEP E: (S)—N-(3-(1H-indol-2-yl)propyl)-2-aminobutanamide

A 20 mL cintillation vial was charged with (S)—N-(3-(1H-indol-2-yl)propyl)-2-(2,2,2-trifluoroacetamido)butanamide (48.2 mg, 0.136 mmol), tetrahydrofuran (0.68 mL), and methanol (0.18 mL). 3N Sodium hydroxide (0.14 mL, 0.407 mmol) was added and the resulting mixture stirred at room temperature for 18 h. The resulting mixture was then diluted with dichloromethane and extracted with 1 N HCl. The aqueous layer was neutralized to pH 8 and extracted with dichlormethane. The organic layer was dried with MgSO$_4$, filtered, and concentrated in vacuo. The resulting solid was taken up in water and lyophilized to yield (S)—N-(3-(1H-indol-2-yl)propyl)-2-aminobutanamide. $^1$H NMR (300 MHz, CDCl$_3$) δ7.52 (d, J=7.6 Hz, 1H), 7.38 (d, J=8.0 Hz, 1H), 7.01-7.13 (m, 2H), 6.22 (s, 1H), 3.30-3.49 (m, 3H), 2.72-2.77 (m, 2H), 1.83-1.96 (m, 3H), 1.58-1.66 (m, 1H), and 0.98 (t, J=7.4 Hz, 3H); MS (ES$^+$) 260 (M+1).

EXAMPLE 2

(S)-2-amino-N-(3-(1-methyl-1H-indol-2-yl)propyl)butanamide (Compound #41)

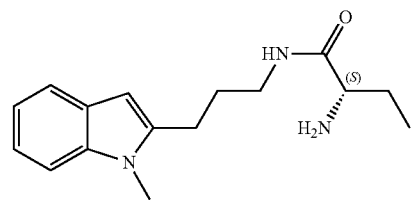

STEP A: N-[3-(1-methyl-1H-indol-2-yl)-propyl]-2-(S)-(2,2,2-trifluoro-acetylamino)-butyramide A 20 mL cintillation vial was charged with (S)—N-(3-(1H-indol-2-yl)propyl)-2-(2,2,2-trifluoroacetamido)butanamide (60 mg, 0.169 mmol) and dimethylformamide (0.75 mL). Sodium hydride (6.0 mg, 0.25 mmol) was added and the resulting mixture was stirred at room temperature for 15 minutes. Methyl iodide (0.012 mL, 0.193 mmol) was added and the resulting mixture was stirred at room temperature for 1 h. The resulting mixture was then concentrated in-vacuo and purified via flash silica gel chromatography (Analogix IF-280, SF25-40 g column, gradient 90:10-50:50 Heptane:EtOAc) to yield N-[3-(1-methyl-1H-indol-2-yl)-propyl]-2-(S)-(2,2,2-trifluoro-acetylamino)-butyramide. $^1$H NMR (300 MHz, CDCl$_3$) δ7.52 (d, J=7.7 Hz, 1H), 7.25-7.28 (m, 1H), 7.14-7.19 (m, 1H), 7.04-7.10 (m, 1H), 6.26 (s, 1H), 4.31-4.36 (m, 1H), 3.64 (s, 3H), 3.33-3.46 (m, 2H), 2.75-2.82 (m, 2H), 1.80-2.09 (m, 3H), 1.59-1.71 (m, 1H), and 0.87-0.92 (m, 3H); MS (ES$^+$) 370 (M+1).

STEP B: (S)-2-amino-N-(3-(1-methyl-1H-indol-2-yl)propyl)butanamide

A 20 mL cintillation vial was charged with N-(3-(1-methyl-1H-indol-2-yl)propyl)-2-(S)-(2,2,2-trifluoro-acetylamino)butanamide (57.0 mg, 0.154 mmol), tetrahydrofuran (0.77 mL), and methanol (0.20 mL). 3N Sodium hydroxide (0.15 mL, 0.450 mmol) was added and the resulting mixture stirred at room temperature for 18 h. The resulting mixture was then diluted with dichloromethane and extracted with 1 N HCl. The aqueous layer was neutralized to pH 8 and extracted with dichlormethane. The organic layer was dried with MgSO$_4$, filter, and concentrate in vacuo. The resulting solid was taken up in water and lyophilized to yield (S)-2-amino-N-(3-(1-methyl-1H-indol-2-yl)propyl)butanamide. $^1$H NMR (300 MHz, CD$_3$OD) δ 7.42 (d, J=7.7 Hz, 1H), 7.29 (d, J=8.0 Hz, 1H), 7.05-7.11 (m, 1H), 6.94-7.02 (m, 1H), 6.23 (s, 1H), 3.60-3.75 (m, 4H), 3.31-3.46 (m, 2H), 2.69-2.86 (m, 2H), 1.91-2.03 (m, 2H), 1.71-1.89 (m, 2H), and 1.02 (t, J=7.4 Hz, 3H); MS (ES$^+$) 274 (M+1).

Representative compounds of the present invention, listed in Table 5 below, with their corresponding, measured MS (ES$^+$) (M+1) mass spec numbers, were similarly prepared according to the procedures described in Examples 1 and 2 above, by selecting and substituting suitably substituted reagent.

TABLE 5

Representative Compounds of Formula (I)

| ID No. | MS (MH+) |
|---|---|
| 1 | 355 |
| 35 | 315 |
| 40 | 260 |
| 41 | 274 |
| 42 | 261 |
| 49 | 306 |
| 56 | 329 |

EXAMPLE 3

2-(S)-Amino-N-[3-(1H-indol-3-yl)-propyl]-butyramide (Compound #44)

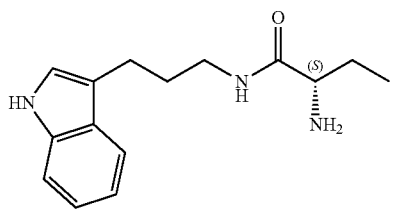

STEP A: (S)-tert-butyl 1-(allylamino)-1-oxobutan-2-ylcarbamate

A 500 mL round bottom flask was charged with (S)-2-(tert-butoxycarbonylamino)butanoic acid (5.0 g, 0.025 mol), 1-hydroxybenzotriazole hydrate (3.4 g, 0.025 mol), N-(3-dimethylaminopropyl)-N'-ethylcarbodiimide hydrochloride (7.2 g, 0.038 mol), and dichloromethane (125 mL). Triethylamine (7.6 mL, 0.055 mol) and allylamine (1.9 g, 0.025 mol) were added and the resulting mixture stirred at room temperature for 22 h. The resulting mixture was then diluted with dichloromethane (300 mL), washed 1× with 1N HCl (200 mL), 1× with 1N NaOH (200 mL), and 1× with water (200 mL). The organic layer was dried with sodium sulfate, filtered, and concentrated in vacuo to yield (S)-tert-butyl 1-(allylamino)-1-oxobutan-2-ylcarbamate. $^1$H NMR (300 MHz, CDCl$_3$) δ 5.77-5.88 (m, 1H), 5.15-5.23 (m, 2H), 4.03-4.19 (m, 1H), 3.88-3.92 (m, 2H), 1.82-1.94 (m, 1H), 1.60-1.72 (m, 1H), 1.45 (s, 9H), and 0.96 (t, J=7.4 Hz, 3H).

STEP B: (S,E)-tert-butyl 3-(3-(2-(tert-butoxycarbonylamino)butanamido)prop-1-enyl)-1H-indole-1-carboxylate A 50 mL sealed tube was charged with (S)-tert-butyl 1-(allylamino)-1-oxobutan-2-ylcarbamate (500 mg, 2.07 mmol), 3-bromo-indole-1-carboxylic acid tert-butyl ester (620 mg, 2.09 mmol), palladium (II) acetate (59 mg, 0.263 mmol), tri-o-tolylphosphine (180 mg, 0.591), acetonitrile (10 mL), and triethylamine (0.6 mL, 4.30 mmol). The tube was flushed with argon and sealed, then stirred and heated to 90° C. for 24 h. The resulting mixture was concentrated in vacuo and the resulting residue purified via flash silica gel chromatography (Analogix IF-280, SF65-150 g column, gradient 90:10-50:50 Heptane:EtOAc) to yield (S,E)-tert-butyl 3-(3-(2-(tert-butoxycarbonylamino)butanamido)prop-1-enyl)-1H-indole-1-carboxylate. $^1$H NMR (300 MHz, CDCl$_3$) δ 7.58 (s, 1H), 7.23-7.36 (m, 4H), 6.60-6.66 (m, 1H), 6.20-6.51 (m, 1H), 4.05-4.11 (m, 1H), 3.86-3.91 (m, 2H), 1.83-1.93 (m, 1H), 1.59-1.72 (m, 1H), 1.44 (s, 18H), and 0.95 (t, J=7.4 Hz, 3H).

STEP C: 3-[3-(2-(S)-tert-Butoxycarbonylamino-butyrylamino)-propyl]-indole-1-carboxylic acid tert-butyl ester A 250 mL Parr hydrogenation vessel was charged with (S,E)-tert-butyl 3-(3-(2-(tert-butoxycarbonylamino)butanamido)prop-1-enyl)-1H-indole-1-carboxylate (280 mg, 0.42 mmol), 10% palladium on carbon (34 mg), and ethanol (6.0 mL). The vessel was evacuated and filled with hydrogen. This was repeated two more times. The vessel was then filled with 50 psi hydrogen. After 24 h, the resulting solution was filtered through CELITE and the filtrate concentrated in vacuo to yield 3-[3-(2-(S)-tert-butoxycarbonylamino-butyrylamino)-propyl]indole-1-carboxylic acid tert-butyl ester. $^1$H NMR (300 MHz, CDCl$_3$) δ 7.21-7.24 (m, 1H), 7.07-7.12 (m, 1H), 6.64-6.71 (m, 1H), 6.42-6.46 (m, 1H), 4.38-4.45 (m, 1H), 3.39-3.53 (m, 2H), 2.53 (t, J=6.8 Hz, 2H), 1.67-1.96 (m, 4H), and 0.88-0.93 (m, 3H).

STEP D: 2-(S)-Amino-N-[3-(1H-indol-3-yl)-propyl]-butyramide

A 20 mL cintillation vial was charged with 3-[3-(2-(S)-tert-butoxycarbonylamino-butyrylamino)-propyl]-indole-1-carboxylic acid tert-butyl ester (280 mg, 0.61 mmol), dichloromethane (3.6 mL), and 1M hydrogen chloride in diethyl ether (3.0 mL). The resulting mixture was stirred at room temperature for 4 h, then concentrated in-vacuo and the residue placed under high vacuum overnight to yield 2-(S)-amino-N-[3-(1H-indol-3-yl)-propyl]-butyramide. $^1$H NMR (300 MHz, CD$_3$OD) δ 7.51 (d, J=7.8 Hz, 1H), 7.32 (d, J=8.0 Hz, 1H), 6.95-7.09 (m, 3H), 3.11-3.39 (m, 3H), 2.77-2.82 (m, 2H), 1.78-2.01 (m, 4H), and 0.94 (t, J=7.4 Hz, 3H); MS (ES$^+$) 260 (M+1).

Compound #43 was similarly prepared according to the procedure described in Example 3 above, with a measured MS (ES$^+$) of 277 (M+1).

EXAMPLE 4

(S)-2-(3-(2-(tert-butoxycarbonylamino)butanamido)propyl)-1H-indole-5-carboxylic acid (Compound #47)

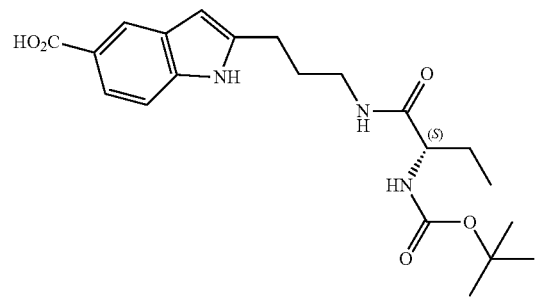

STEP A: (1-Pent-4-ynylcarbamoyl-propyl)-(S)-carbamic acid tert-butyl ester

A 500 mL round bottom flask was charged with (S)-2-(tert-butoxycarbonylamino)butanoic acid (5.0 g, 0.025 mol), 1-hydroxybenzotriazole hydrate (4.5 g, 0.033 mol), N-(3-dimethylaminopropyl)-N'-ethylcarbodiimide hydrochloride (6.4 g, 0.033 mol), 4-(dimethylamino)pyridine (0.02 g, 0.163 mmol), and dimethylformamide (95 mL). Triethylamine (10.6 mL, 0.076 mol) and pent-4-yn-1-amine (2.7 g, 0.033 mol) were added and the resulting mixture was stirred at room temperature for 22 h. The resulting mixture was concentrated in vacuo and the residue purified via flash silica gel chromatography (Analogix IF-280, SF65-400 g column, gradient 90:10-40:60 Heptane:EtOAc) to yield (1-pent-4-ynylcarbamoyl-propyl)-(S)-carbamic acid tert-butyl ester. $^1$H NMR (300 MHz, CDCl$_3$) δ 3.93-4.00 (m, 1H), 3.36-3.42 (m, 2H), 2.22-2.28 (m, 2H), 2.00 (s, 1H), 1.83-1.92 (m, 1H), 1.70-1.80 (m, 2H), 1.57-1.67 (m, 1H), 1.45 (s, 9H), and 0.94 (t, J=7.4 Hz, 3H).

STEP B: 4-Amino-3-[5-(2-(S)-tert-butoxycarbonylamino-butyrylamino)-pent-1-ynyl]-benzoic acid methyl ester A 50 mL round bottom flask was charged with (1-pent-4-ynylcarbamoyl-propyl)-(S)-carbamic acid tert-butyl ester (2.24 g, 8.36 mmol), methyl 4-amino-3-iodobenzoate (2.38 g, 8.59 mmol), copper iodide (0.21 g, 1.10 mmol), palladium tetrakistriphenylphosphine (1.12 g, 0.97 mmol), and diethylamine (300 mL). The resulting mixture was stirred at room temperature for 4 h, then concentrated in vacuo and the resulting residue purified via flash silica gel chromatography (Analogix IF-280, SF40-400 g column, gradient 90:10-10:90 Heptane:EtOAc) to yield 4-amino-3-[5-(2-(S)-tert-butoxycarbonylamino-butyrylamino)-pent-1-ynyl]-benzoic acid methyl ester. $^1$H NMR (300 MHz, CDCl$_3$) δ 7.94 (s, 1H), 7.76 (d, J=6.5 Hz, 1H), 6.64 (d, J=8.5 Hz, 1H), 3.91-4.09 (m, 1H), 3.85 (s, 3H), 3.47-3.52 (m, 2H), 2.52 (t, J=6.8 Hz, 2H), 1.75-1.92 (m, 3H), 1.60-1.69 (m, 1H), 1.44 (s, 9H), and 0.94 (t, J=7.4 Hz, 3H).

STEP C: (S)-Methyl 2-(3-(2-(tert-butoxycarbonylamino)butanamido)propyl)-1H-indole-5-carboxylate A 250 mL round bottom flask was charged with 4-amino-3-[5-(2-(S)-tert-butoxycarbonylamino-butyrylamino)-pent-1-ynyl]-benzoic acid methyl ester (2.51 g, 6.02 mmol), dichlorobis(benzonitrile)palladium (II) (490 mg, 1.28 mmol), and dimethylformamide (67 mL) and the resulting mixture heated to 80° C. for 24 h. The resulting mixture was then concentrated in-vacuo and the residue purified via flash silica gel chromatography (Analogix IF-280, SF25-40 g column, gradient 90:10-30:70 Heptane:EtOAc) to yield (S)-methyl 24342-(tert-butoxycarbonylamino)butanamido)propyl)-1H-indole-5-carboxylate. $^1$H NMR (300 MHz, CDCl$_3$) δ 8.29 (s, 1H), 7.83 (d, J=8.0 Hz, 1H), 7.39 (d, J=8.4 Hz, 1H), 6.31 (s, 1H), 3.95-4.02 (m, 1H), 3.92 (s, 3H), 3.33-3.53 (m, 2H), 2.74-2.87 (m, 2H), 1.81-1.99 (m, 3H), 1.60-1.75 (m, 1H), 1.45 (s, 9H), and 0.99 (t, J=7.4 Hz, 3H); MS (ES$^+$) 418 (M+1).

STEP D: (S)-2-(3-(2-(tert-butoxycarbonylamino)butanamido)propyl)-1H-indole-5-carboxylic acid A 200 mL round bottom flask was charged with (S)-methyl 2-(3-(2-(tert-butoxycarbonylamino)butanamido)propyl)-1H-indole-5-carboxylate (1.67 g, 4.00 mmol), tetrahydrofuran (20 mL), and methanol (5.3 mL). 3N Sodium hydroxide (4.0 mL, 12.0 mmol) was added and the resulting mixture stirred and heated to 50° C. for 8 h. The resulting mixture was then cooled to room temperature and acidified with 1N hydrochloric acid. The resulting mixture was extracted two times with ethyl acetate (400 mL). The organic layer was dried with MgSO$_4$, filtered, and concentrated in vacuo to yield (S)-2-(3-(2-(tert-butoxycarbonylamino)butanamido)propyl)-1H-indole-5-carboxylic acid. $^1$H NMR (300 MHz, CD$_3$OD) δ 8.20 (s, 1H), 7.75 (d, J=7.0 Hz, 1H), 7.32 (d, J=8.6 Hz, 1H), 6.31 (s, 1H), 3.94-4.10 (m, 1H), 3.22-3.34 (m, 2H), 2.80-2.85 (m, 2H), 1.61-2.08 (m, 4H), 1.46 (s, 9H), and 0.93-1.03 (m, 3H); MS (ES$^+$) 403 (M+1).

EXAMPLE 5

(S)-2-(3-(2-aminobutanamido)propyl)-N-(3,4-dimethoxyphenyl)-1H-indole-5-carboxamide (Compound #50)

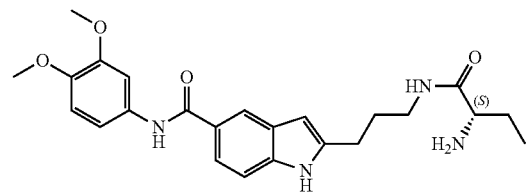

STEP A: (1-{3-[5-(3,4-Dimethoxy-phenylcarbamoyl)-1H-indol-2-yl]-propylcarbamoyl}-propyl)-(S)-carbamic acid tert-butyl ester A 50 mL round bottom flask was charged with (S)-2-(3-(2-(tert-butoxycarbonylamino)butanamido)propyl)-1H-indole-5-carboxylic acid (740 mg, 1.84 mmol), bis(2-oxo-3-oxazolidinyl)phosphinic chloride (530 mg, 2.08 mmol), and dichloromethane (10.6 mL). Triethylamine (0.8 mL, 5.74 mmol) was added and the resulting mixture was stirred at room temperature for 15 minutes. 3,4-dimethoxyaniline (290 mg, 1.89 mmol) was added and the resulting mixture was stirred at room temperature for 23 h. The resulting mixture was then concentrated in-vacuo and the residue purified via flash silica gel chromatography (Analogix IF-280, SF40-115 g column, gradient 100:0-94:6 CH$_2$Cl$_2$:MeOH) to yield (1-{3-[5-(3,4-dimethoxy-phenylcarbamoyl)-1H-indol-2-yl]-propylcarbamoyl}-propyl)-(S)-carbamic acid tert-butyl ester. $^1$H NMR (300 MHz, CDCl$_3$) δ 7.85-7.89 (m, 1H), 7.58 (d, J=8.4 Hz, 1H), 7.43 (s, 1H), 7.20-7.30 (m, 2H), 6.83 (d, J=8.8 Hz, 1H), 6.23 (s, 1H), 4.33-4.40 (m, 1H), 3.76 (s, 3H), 3.73 (s, 3H), 3.26-3.40 (m, 2H), 2.56-2.68 (m, 2H), 1.73-1.84 (m, 3H), 1.52-1.67 (m, 1H), 1.36 (s, 9H), and 0.90 (t, J=7.2 Hz, 3H); MS (ES$^+$) 539 (M+1).

STEP B: (S)-2-(3-(2-aminobutanamido)propyl)-N-(3,4-dimethoxyphenyl)-1H-indole-5-carboxamide A 50 mL round bottom flask was charged with (1-{3-[5-(3,4-dimethoxy-phenylcarbamoyl)-1H-indol-2-yl]-propylcarbamoyl}-propyl)-(S)-carbamic acid tert-butyl ester (810 mg, 1.51 mmol) and dichloromethane (7.5 mL). 1M Hydrochloric acid in diethyl ether (7.5 mL) was added and the resulting mixture stirred at room temperature for 40 minutes.

The resulting mixture was then concentrated in vacuo, the residue triturated with diethyl ether, and placed under high vacuum to yield (S)-2-(3-(2-aminobutanamido)propyl)-N-(3,4-dimethoxyphenyl)-1H-indole-5-carboxamide. $^1$H NMR (300 MHz, DMSO) δ 7.85-7.89 (m, 1H), 7.58 (d, J=8.4 Hz, 1H), 7.43 (s, 1H), 7.20-7.30 (m, 2H), 6.83 (d, J=8.8 Hz, 1H), 6.23 (s, 1H), 3.67 (s, 3H), 3.65 (s, 3H), 3.59-3.63 (m, 1H), 3.04-3.37 (m, 2H), 2.64-2.79 (m, 2H), 1.80-1.96 (m, 2H), 1.62-1.77 (m, 2H), and 0.97 (t, J=7.2 Hz, 3H); MS (ES$^+$) 439 (M+1); Anal. Calcd for $C_{24}H_{30}N_4O_4 \cdot 1.1$ HCl$\cdot$0.7; $H_2O$: C, 58.68; H, 6.67; N, 11.41; Cl, 7.94; $H_2O$, 2.57. Found: C, 58.88; H, 6.98; N, 11.73; Cl, 7.50; $H_2O$, 2.32.

Representative compounds of the present invention, listed in Table 6 below, with their corresponding, measured MS (ES$^+$) (M+1) mass spec numbers, were similarly prepared according to the procedures described in Examples 4 and 5 above, by selecting and substituting suitably substituted reagent.

TABLE 6

Representative Compounds of Formula (I)

| ID No. | MH$^+$ |
| --- | --- |
| 7 | 533 |
| 47 | 403 |
| 48 | 370 |
| 51 | 380 |
| 52 | 381 |
| 53 | 394 |
| 54 | 430 |
| 55 | 431 |
| 57 | 437 |
| 58 | 440 |
| 59 | 434 |
| 61 | 369 |
| 62 | 445 |
| 63 | 421 |
| 64 | 431 |
| 65 | 431 |
| 66 | 431 |
| 67 | 431 |
| 68 | 431 |
| 69 | 438 |
| 70 | 424 |
| 71 | 420 |
| 72 | 420 |
| 73 | 435 |
| 75 | 393 |
| 76 | 414 |
| 77 | 409 |
| 78 | 435 |
| 79 | 397 |
| 80 | 421 |
| 81 | 415 |
| 82 | 448 |
| 83 | 407 |
| 84 | 420 |
| 85 | 420 |
| 86 | 468 |
| 87 | 397 |
| 88 | 409 |
| 89 | 421 |
| 90 | 397 |
| 91 | 414 |
| 92 | 409 |
| 93 | 393 |
| 94 | 440 |
| 95 | 408 |
| 97 | 507 |

EXAMPLE 6

(S)-2-amino-1-(4-(5-(3,4-dimethoxyphenyl)-1H-indol-2-yl)piperidin-1-yl)-3-(thiophen-2-yl)propan-1-one (Compound #2)

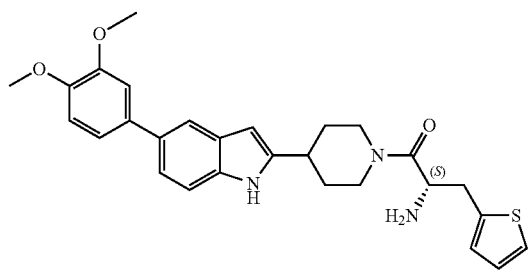

STEP A: 4-(2-Amino-5-bromo-phenylethynyl)-piperidine-1-carboxylic acid tert-butyl ester A 50 mL round bottom flask was charged with tert-butyl 4-ethynylpiperidine-1-carboxylate (3.51 g, 16.8 mmol), methyl 4-amino-3-iodobenzoate (5.0 g, 16.8 mmol), copper iodide (0.35 g, 1.85 mmol), palladium tetrakistriphenylphosphine (1.94 g, 1.68 mmol), and diethylamine (560 mL) and the resulting mixture stirred at room temperature for 24 h. The resulting mixture was then concentrated in vacuo and the residue purified via flash silica gel chromatography (Analogix IF-280, SF40-400 g column, gradient 90:10-70:30 Heptane:EtOAc) to yield 4-(2-amino-5-bromo-phenylethynyl)-piperidine-1-carboxylic acid tert-butyl ester. MS (ES$^+$) 380 (M+1).

STEP B: tert-Butyl 4-(5-bromo-1H-indol-2-yl)piperidine-1-carboxylate

A 250 mL round bottom flask was charged with 4-(2-amino-5-bromo-phenylethynyl)-piperidine-1-carboxylic acid tert-butyl ester (5.90 g, 15.6 mmol), dichlorobis(benzonitrile)palladium (II) (1.20 g, 3.13 mmol), and dimethylformamide (175 mL) and the resulting mixture heated to 80° C. for 24 h. The resulting mixture was then concentrated in-vacuo and the residue purified via flash silica gel chromatography (Analogix IF-280, SF25-40 g column, gradient 90:10-80:20 Heptane:EtOAc) to yield tert-butyl 4-(5-bromo-1H-indol-2-yl)piperidine-1-carboxylate. $^1$H NMR (300 MHz, CDCl$_3$) δ 7.66 (s, 1H), 7.16-7.23 (m, 2H), 6.20 (s, 1H), 2.84-3.02 (m, 5H), 1.97-2.04 (m, 2H), 1.61-1.74 (m, 2H), and 1.48 (s, 9H); MS (ES$^+$) 380 (M+1).

STEP C: 4-[5-(3,4-Dimethoxy-phenyl)-1H-indol-2-yl]-piperidine-1-carboxylic acid tert-butyl ester A 100 mL sealed tube was charged with tert-butyl 4-(5-bromo-1H-indol-2-yl)piperidine-1-carboxylate (1.04 g, 2.74 mmol), 3,4-dimethoxyphenylboronic acid (0.58 g, 3.19 mmol), 1,1'-bis(di-t-butylphosphino)ferrocene palladium dichloride (0.11 g, 0.169 mmol), 10% aqueous sodium carbonate (6.1 mL), and 1,4-dioxane (13.2 mL). The vessel was then flushed with argon and sealed. The resulting mixture was stirred at 100° C. for 24 h, then diluted mixture with dichloromethane (300 mL) and washed with water (100 mL). The organic layer was dried with MgSO$_4$, filtered, and concentrated in vacuo to yield 4-[5-(3,4-cimethoxy-phenyl)-1H-indol-2-yl]-piperidine-1-carboxylic acid tert-butyl ester. $^1$H NMR (300 MHz, CD$_3$OD) δ 7.71 (s, 1H), 7.33-7.38 (m, 2H), 7.15-7.24 (m, 2H), 6.95 (d, J=8.0 Hz, 1H), 6.31 (s, 1H), 3.96 (s, 3H), 3.93 (s, 3H), 2.85-2.93 (m, 5H), 2.02-2.11 (m, 2H), 1.65-1.77 (m, 2H), and 1.49 (s, 9H); MS (ES$^+$) 437 (M+1).

STEP D: 5-(3,4-Dimethoxyphenyl)-2-(piperidin-4-yl)-1H-indole

A 50 mL round bottom flask was charged with 4-[5-(3,4-dimethoxy-phenyl)-1H-indol-2-yl]-piperidine-1-carboxylic acid tert-butyl ester (500 mg, 1.15 mmol), dichloromethane (5.8 mL), and 1M hydrochloric acid in diethyl ether (5.8 mL) and the resulting mixture stirred for 2 h. The resulting mixture was then concentrated in vacuo, the residue triturated with diethyl ether, and then placed under high vacuum to yield 5-(3,4-dimethoxyphenyl)-2-(piperidin-4-yl)-1H-indole. $^1$H NMR (300 MHz, DMSO-d$_6$) δ 7.69 (s, 1H), 7.29-7.37 (m, 2H), 7.09-7.22 (m, 2H), 6.99 (d, J=8.2 Hz, 1H), 6.22 (s, 1H), 3.84 (s, 3H), 3.78 (s, 3H), 3.67-3.74 (m, 1H), 3.02-3.15 (m, 4H), 2.50-2.61 (m, 2H), and 1.81-2.01 (m, 2H); MS (ES$^+$) 337 (M+1).

STEP E: (2-{4-[5-(3,4-Dimethoxy-phenyl)-1H-indol-2-yl]-piperidin-1-yl}-2-oxo-1-thiophen-2-ylmethyl-ethyl)-(S)-carbamic acid tert-butyl ester A 50 mL round bottom flask was charged with (S)-2-(tert-butoxycarbonylamino)-3-(thiophen-2-yl)propanoic acid (42.1 mg, 0.155 mmol), 1-hydroxybenzotriazole hydrate (27.3 mg, 0.201 mmol), N-(3-dimethylaminopropyl)-N'-ethylcarbodiimide hydrochloride (38.6 mg, 0.201 mmol), 4-(dimethylamino)pyridine (1.0 mg, 0.008 mmol), and dimethylformamide (2.0 mL). Triethylamine (0.07 mL, 0.502 mmol) and 5-(3,4-dimethoxyphenyl)-2-(piperidin-4-yl)-1H-indole (77.0 mg, 0.207 mmol) were added and the resulting mixture stirred at room temperature for 22 h. The resulting mixture was then concentrated in vacuo and the residue purified via flash silica gel chromatography (ISCO, SF25-40 g column, gradient 90:10-75:25 Heptane:EtOAc) to yield (2-{4-[5-(3,4-dimethoxy-phenyl)-1H-indol-2-yl]piperidin-1-yl}-2-oxo-1-thiophen-2-ylmethyl-ethyl)-(S)-carbamic acid tert-butyl ester. $^1$H NMR (300 MHz, CDCl$_3$) δ 7.7 (s, 1H), 7.4 (m, 2H), 7.2 (m, 3H), 7.0 (m, 3H), 6.99 (d, J=8.2 Hz, 1H), 6.22 (s, 1H), 5.4 (m, 1H), 4.6-4.9 (m, 2H), 4.0 (s, 3H), 3.9 (s, 3H), 3.1-3.3 (m, 4H), 2.78 (m, 1H), 1.4-1.6 (m, 4H); MS (ES$^+$) 590 (M+1).

STEP F: (S)-2-amino-1-(4-(5-(3,4-dimethoxyphenyl)-1H-indol-2-yl)piperidin-1-yl)-3-(thiophen-2-yl)propan-1-one A 50 mL round bottom flask was charged with (1-{3-[5-(3,4-dimethoxy-phenylcarbamoyl)-1H-indol-2-yl]-propylcarbamoyl}-propyl)-(S)-carbamic acid tert-butyl ester (69.0 mg, 0.117 mmol) and dichloromethane (1 mL). 1M Hydrochloric acid in diethyl ether (3 mL) was added and the resulting mixture stirred at room temperature for 3 h. The resulting mixture was then concentrated in vacuo and the residue (an oil) was purified on a Gilson HPLC with a reversed phase Kromasil column (10u, 100 Å C18, column length 250×50 mm, gradient 80:20-0:100 H$_2$O:MeCN). The resulting solid was taken up in dichloromethane and treated with 1M hydrochloric acid in diethyl ether. The resulting mixture was concentrated in vacuo. This procedure was repeated two more times to yield (S)-2-amino-1-(4-(5-(3,4-dimethoxyphenyl)-1H-indol-2-yl)piperidin-1-yl)-3-(thiophen-2-yl)propan-1-one. $^1$H NMR (300 MHz, DMSO) δ 7.73 (m, 1H), 7.35-7.78 (m, 3H), 7.43 (s, 1H), 7.12-7.30 (m, 2H), 6.83-7.01 (m, 3H), 6.15 (s, 1H), 4.42-4.53 (m, 2H), 3.95 (m, 1H), 3.81 (s, 3H), 3.62 (s, 3H), 3.11-3.25 (m, 4H), 3.01 (m, 1H), 2.41 (m, 2H), 1.81 (m, 2H); MS (ES$^+$) 490 (M+1).

Representative compounds of the present invention, listed in Table 7 below with their corresponding measured MS (ES$^+$) (M+1) mass spec numbers, were similarly prepared according to the procedures described in Example 6 above, by selecting and substituting suitably substituted reagent.

TABLE 7

Representative Compounds of Formula (I)

| ID No. | MH$^+$ |
|---|---|
| 3 | 488 |
| 4 | 460 |
| 5 | 473 |
| 6 | 474 |
| 9 | 422 |
| 10 | 569 |
| 11 | 474 |
| 12 | 462 |
| 13 | 474 |
| 14 | 488 |
| 15 | 490 |
| 20 | 455 |
| 21 | 474 |
| 23 | 431 |
| 24 | 525 |
| 25 | 461 |
| 26 | 431 |
| 45 | 337 |
| 96 | 396 |
| 100 | 336 |
| 101 | 354 |
| 102 | 404 |
| 103 | 379 |
| 104 | 366 |
| 105 | 420 |
| 109 | 472 |
| 111 | 379 |
| 112 | 380 |
| 113 | 415 |
| 114 | 337 |
| 116 | 379 |

EXAMPLE 7

(S)-2-(3-(2-amino-3-(thiazol-2-yl)propanamido)propyl)-N-(3,4-dimethoxyphenyl)-1H-indole-5-carboxamide (Compound #117)

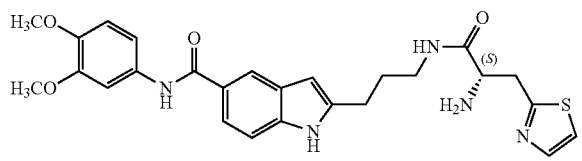

STEP A: 2-(S)-tert-Butoxycarbonylamino-3-thiocarbamoyl-propionic acid benzyl ester A 1-L round bottom flask was charged with (S)-benzyl 4-amino-2-(tert-butoxycarbonylamino)-4-oxobutanoate (10.0 g, 31.0 mmol), Lawesson's reagent (6.58 g, 16.3 mmol), and tetrahydrofuran (155 mL). Hydrazine (7.8 mL, 0.248 mol) was added and the resulting mixture was stirred at room temperature for 72 h. The resulting mixture was then concentrated in vacuo and the residue purified via flash silica gel chromatography (Analogix IF-280, SF40-400 g column, gradient 90:10-60:40 Heptane:EtOAc) to yield-(S)-tert-butoxycarbonylamino-3-thiocarbamoyl-propionic acid benzyl ester. MS (ES$^+$) 339 (M+1).

STEP B: 2-(S)-tert-Butoxycarbonylamino-3-thiazol-2-yl-propionic acid benzyl ester A 250 mL round bottom flask was charged with 2-(S)-tert-butoxycarbonylamino-3-thiocarbamoyl-propionic acid benzyl ester (1.0 g, 2.96 mmol), dimethoxyethane (66 mL), and bromoacetate diethylacetal (2.4 mL, 15.5 mmol). The flask containing the resulting mixture was fit with a reflux condenser and the mixture refluxed for 3 h. The resulting mixture was then concentrated in vacuo and the residue purified via flash silica gel chromatography (Analogix IF-280, SF65-400 g column, gradient 100:0-90:10 $CH_2Cl_2$:MeOH) to yield 2-(S)-tert-butoxycarbonylamino-3-thiazol-2-yl-propionic acid benzyl ester. $^1$H NMR (300 MHz, CDCl$_3$) δ 7.67 (d, J=3.3 Hz, 1H), 7.29-7.44 (m, 5H), 7.20 (d, J=3.3 Hz, 1H), 5.15 (s, 2H), 5.75 (t, J=5.5 Hz, 1H), 73.15 (d, J=7.4 Hz, 1H), and 1.44 (s, 9H); MS (ES$^+$) 363 (M+1).

STEP C: (S)-2-(tert-butoxycarbonylamino)-3-(thiazol-2-yl)propanoic acid

A 100 mL round bottom flask was charged with 2-(S)-tert-butoxycarbonylamino-3-thiazol-2-yl-propionic acid benzyl ester (370 mg, 1.02 mmol), tetrahydrofuran (9.0 mL), water (0.9 mL), and lithium hydroxide (48 mg, 1.14 mmol) and the resulting mixture was stirred at room temperature for 6 h. The resulting mixture was then neutralized with 10% citric acid and extracted with ethyl acetate (100 mL), and dichlormethane (100 mL). The organic layers were dried with MgSO$_4$, filtered, and concentrated in vacuo to yield (S)-2-(tert-butoxycarbonylamino)-3-(thiazol-2-yl)propanoic acid. MS (ES$^+$) 273 (M+1).

STEP D: 4-Amino-N-(3,4-dimethoxyphenyl)-3-iodobenzamide

A 500 mL round bottom flask was charged with methyl 4-amino-3-iodobenzoate (10.0 g, 36.1 mmol), methanol (270 mL), water (30 mL), and lithium hydroxide (1.82 g, 43.3 mmol). The vessel was flushed with nitrogen, fit with a reflux condenser, and the mixture heated to a gentle reflux for 20 h. The resulting mixture was then cooled to room temperature, acidify with 2N hydrochloric acid, then concentrated in vacuo. A 500 mL round bottom flask was charged with the resulting solid (9.5 g, 36.7 mmol) and dichloromethane (180 mL) was added. Bis(2-oxo-3-oxazolidinyl)phosphinic chloride (10.0 g, 39.5 mmol) and triethylamine (11.1 mL, 79.2 mmol) were added. 3,4-Dimethoxyaniline (11.1 g, 72.1 mmol) was then added and the resulting mixture was stirred at room temperature for 24 h. The resulting mixture was then diluted with ethyl acetate and washed with 1N NaOH. The organic layer was dried with MgSO$_4$, filter, then concentrate in vacuo to yield 4-amino-N-(3,4-dimethoxyphenyl)-3-iodobenzamide. $^1$H NMR (300 MHz, CDCl$_3$) δ 8.23 (s, 1H), 7.73 (d, J=8.5 Hz, 1H), 7.42 (s, 1H), 7.30 (d, J=8.6 Hz, 1H), 6.90 (d, J=8.8 Hz, 1H), 6.77 (d, J=8.5 Hz, 1H), 3.74 (s, 3H), and 3.72 (s, 3H).

STEP E: Pent-4-ynyl-carbamic acid tert-butyl ester

A 1-L round bottom flask was charged with pent-4-yn-1-amine (10.0 g, 0.120 mol), dichloromethane (600 mL), and triethylamine (33.6 mL, 0.241 mol). The resulting mixture was cooled with an ice/water bath. Additional di-tert-butyl dicarbonate (38.4 g, 0.176 mol) was added in 3 portions and the resulting mixture stirred at room temperature for 72 h. The resulting mixture was then concentrated in vacuo and the residue purified via flash silica gel chromatography (Analogix IF-280, SF65-400 g column, gradient 90:10-80:20 heptane:EtOAc) to yield pent-4-ynyl-carbamic acid tert-butyl ester. $^1$H NMR (300 MHz, CDCl$_3$) δ 3.20-3.26 (m, 2H), 2.21-2.27 (m, 2H), 1.97 (s, 1H), 1.67-1.82 (m, 2H), and 1.44 (s, 9H).

STEP F: {5-[2-Amino-5-(3,4-dimethoxy-phenylcarbamoyl)-phenyl]-pent-4-ynyl}-carbamic acid tert-butyl ester A 500 mL round bottom flask was charged with pent-4-ynyl-carbamic acid tert-butyl ester (1.35 g, 7.37 mmol), 4-amino-N-(3,4-dimethoxyphenyl)-3-iodobenzamide (1.35 g, 6.98 mmol), copper iodide (0.16 g, 0.814 mmol), palladium tetrakistriphenylphosphine (0.81 g, 0.701 mmol), and diethylamine (230 mL) and the resulting mixture stirred at room temperature for 24 h. The resulting mixture was then concentrated in vacuo and the residue purified via flash silica gel chromatography (Analogix IF-280, SF40-400 g column, gradient 90:10-10:90 Heptane:EtOAc) to yield {5-[2-amino-5-(3,4-dimethoxy-phenylcarbamoyl)-phenyl]-pent-4-ynyl}-carbamic acid tert-butyl ester. MS (ES$^+$) 454 (M+1).

STEP G: tert-Butyl 3-(5-(3,4-dimethoxyphenylcarbamoyl)-1H-indol-2-yl)propylcarbamate A 500 mL round bottom flask was charged with {5-[2-amino-5-(3,4-dimethoxy-phenylcarbamoyl)-phenyl]-pent-4-ynyl}-carbamic acid tert-butyl ester (3.0 g, 6.62 mmol), dichlorobis(benzonitrile)palladium (II) (0.514 g, 1.34 mmol), and dimethylformamide (80 mL) and the resulting mixture heated to 80° C. for 24 h. The resulting mixture was then concentrated in-vacuo and the residue via flash silica gel chromatography (Analogix IF-280, SF25-40 g column, gradient 100:0-90:10 $CH_2Cl_2$:MeOH) to yield tert-butyl 3-(5-(3,4-dimethoxyphenylcarbamoyl)-1H-indol-2-yl)propylcarbamate. MS (ES$^+$) 454 (M+1); HPLC: Kromasil C18 column (50×2 mm; 3.5μ), gradient 1090% (MeCN+0.16% TFA) in (water+0.2% TFA) over 4 min, $t_R$=3.78 min.

STEP H: 2-(3-Amino-propyl)-1H-indole-5-carboxylic acid (3,4-dimethoxy-phenyl)-amide A 250 round bottom flask was charged with tert-butyl 3-(5-(3,4-dimethoxyphenylcarbamoyl)-1H-indol-2-yl)propylcarbamate (3.0 g, 6.62 mmol), dichloromethane (33 mL), and 1M hydrochloric acid in diethyl ether (33 mL) and the resulting mixture stirred for 2 h. The resulting mixture was then concentrated in vacuo, the residue triturated with diethyl ether, and placed under high vacuum to yield 2-(3-amino-propyl)-1H-indole-5-carboxylic acid (3,4-dimethoxy-phenyl)-amide. MS (ES$^+$) 354 (M+1); HPLC: Kromasil C18 column (50×2 mm; 3.5μ), gradient 10-90% (MeCN+0.16% TFA) in (water+0.2% TFA) over 4 min, $t_R$=2.46 min.

STEP I: (1-{3-[5-(3,4-Dimethoxy-phenylcarbamoyl)-1H-indol-2-yl]-propylcarbamoyl}-2-thiazol-2-yl-ethyl)-(S)-carbamic acid tert-butyl ester A 50 mL round bottom flask was charged with (S)-2-(tert-butoxycarbonylamino)-3-(thiazol-2-yl)propanoic acid (110 mg, 0.404 mmol), 1-hydroxybenzotriazole hydrate (74.8 mg, 0.553 mmol), N-(3-dimethylaminopropyl)-N'-ethylcarbodiimide hydrochloride (198 mg, 1.03 mmol), and dichloromethane (2.2 mL). To the resulting mixture was then added triethylamine (0.22 mL, 1.58 mmol) and 2-(3-amino-propyl)-1H-indole-5-carboxylic acid (3,4-dimethoxy-phenyl)-amide (220 mg, 0.564 mmol). The resulting mixture was stirred at room temperature for 24 h, then concentrated in vacuo and the residue purified using a Gilson HPLC with a reversed phase Kromasil column (10μ, 100 Å C18, column length 250×50 mm, gradient 70:30-0:100 H$_2$O:MeCN) to yield (1-{3-[5-(3,4-dimethoxy-phenylcarbamoyl)-1H-indol-2-yl]propylcarbamoyl}-2-thiazol-2-yl-ethyl)-(S)-carbamic acid tert-butyl ester. MS (ES$^+$) 608 (M+1); HPLC: Kromasil C18 column (50×2 mm; 3.5μ), gradient 1090% (MeCN+0.16% TFA) in (water+0.2% TFA) over 4 min, $t_R$=3.47 min.

STEP J: (S)-2-(3-(2-amino-3-(thiazol-2-yl)propanamido)propyl)-N-(3,4-dimethoxyphenyl)-1H-indole-5-carboxamide A 50 mL round bottom flask was charged with (1-{3-[5-(3,4-dimethoxy-phenylcarbamoyl)-1H-indol-2-yl]-propyl-carbamoyl}-2-thiazol-2-yl-ethyl)-(S)-carbamic acid tert-butyl ester (213.3 mg, 0.351 mmol) and dichloromethane (1.8 mL). 1M Hydrochloric acid in diethyl ether (1.8 mL) was added and the resulting mixture stirred at room temperature for 1.5 h. The resulting mixture was then concentrated in vacuo to yield (S)-2-(3-(2-amino-3-(thiazol-2-yl)propanamido)propyl)-N-(3,4-dimethoxyphenyl)-1H-indole-5-carboxamide. $^1$H NMR (300 MHz, DMSO-d$_6$) δ 8.13 (s, 1H), 7.75-7.87 (m, 1H), 7.61-7.70 (m, 2H), 7.50-7.55 (m, 1H), 7.35-7.45 (m, 2H), 6.91 (d, J=8.8 Hz, 1H), 6.29 (s, 1H), 3.76 (s, 3H), 3.74 (s, 3H), 3.60-3.71 (m, 1H), 3.53 (d, J=6.5 Hz, 2H), 3.01-3.31 (m, 2H), 2.69-2.82 (m, 2H), and 1.76-1.91 (m, 2H); MS (ES$^+$) 508 (M+1).

Representative compounds of the present invention, listed in Table 8 below with their corresponding measured MS (ES$^+$) (M+1) mass spec numbers, were similarly prepared according to the procedures described in Example 7 above, by selecting and substituting suitably substituted reagent.

TABLE 8

Representative Compounds of Formula (I)

| ID No. | MH$^+$ |
|---|---|
| 8 | 474 |
| 17 | 534 |
| 22 | 505 |

EXAMPLE 8

(S)-2-(3-(2-amino-N-methyl-3-(thiophen-2-yl)propanamido)propyl)-N-(3,4-dimethoxyphenyl)-1H-indole-5-carboxamide (Compound #106)

STEP A: Pent-4-ynyl-carbamic acid tert-butyl ester

A 1-L round bottom flask was charged with pent-4-yn-1-amine (10.0 g, 0.120 mol), dichloromethane (600 mL), and triethylamine (33.6 mL, 0.241 mol) and the resulting mixture cooled with an ice/water bath. Di-tert-butyl dicarbonate (38.4 g, 0.176 mol) was added in 3 portions and the resulting mixture stirred at room temperature for 72 h. The resulting mixture was then concentrated in vacuo and the residue purified via flash silica gel chromatography (Analogix IF-280, SF65-400 g column, gradient 90:10-80:20 heptane:EtOAc) to yield pent-4-ynyl-carbamic acid tert-butyl ester. $^1$H NMR (300 MHz, CDCl$_3$) δ 3.20-3.26 (m, 2H), 2.21-2.27 (m, 2H), 1.97 (s, 1H), 1.67-1.82 (m, 2H), and 1.44 (s, 9H).

STEP B: Methyl-pent-4-ynyl-carbamic acid tert-butyl ester

A 500 mL round bottom flask was charged with pent-4-ynyl-carbamic acid tert-butyl ester (5.0 g, 27.3 mmol) and tetrahydrofuran (138 mL) and the resulting mixture cooled with an ice/water bath. Sodium hydride (830 mg, 32.9 mmol) was added in 3 portions and the resulting mixture stirred at room temperature for 20 minutes. Methyl iodide (8.6 mL, 138.1 mmol) was slowly added and the resulting mixture stirred for 72 h. The resulting mixture was diluted with dichlormethane (350 mL), washed with 1N HCl (100 mL), 1N, NaOH (100 mL), and water (100 mL). The organic layer was washed with MgSO$_4$, filtered, then concentrated in vacuo to yield methyl-pent-4-ynyl-carbamic acid tert-butyl ester. $^1$H NMR (300 MHz, CDCl$_3$) δ 3.31 (t, J=7.0 Hz, 2H), 2.86 (s, 3H), 2.17-2.24 (m, 2H), 1.96 (s, 1H), 1.72-1.79 (m, 2H), and 1.46 (s, 9H).

STEP C: {5-[2-Amino-5-(3,4-dimethoxy-phenylcarbamoyl)-phenyl]-pent-4-ynyl}-methyl-carbamic acid tert-butyl ester A 500 mL round bottom flask was charged with methyl-pent-4-ynyl-carbamic acid tert-butyl ester (1.70 g, 8.62 mmol), 4-amino-N-(3,4-dimethoxyphenyl)-3-iodobenzamide (3.0 g, 7.53 mmol), copper iodide (0.225 g, 1.18 mmol), palladium tetrakistriphenylphosphine (0.93 g, 0.805 mmol), and diethylamine (258 mL) and the resulting mixture stirred at room temperature for 24 h. The resulting mixture was then concentrated in vacuo and the residue purified via flash silica gel chromatography (Analogix IF-280, SF40-400 g column, gradient 90:10-10:90 Heptane:EtOAc) to yield {5-[2-amino-5-(3,4-dimethoxy-phenylcarbamoyl)-phenyl]-pent-4-ynyl}-methyl-carbamic acid tert-butyl ester. MS (ES$^+$) 468 (M+1).

STEP D: tert-butyl 3-(5-(3,4-dimethoxyphenylcarbamoyl)-1H-indol-2-yl)propyl(methyl)carbamate A 500 mL round bottom flask was charged with {5-[2-amino-5-(3,4-dimethoxy-phenylcarbamoyl)-phenyl]-pent-4-ynyl}-methyl-carbamic acid tert-butyl ester (3.4 g, 7.27 mmol), dichlorobis(benzonitrile)palladium (II) (0.558 g, 1.45 mmol), and dimethylformamide (80 mL) and the resulting mixture heated to 80° C. for 24 h. The resulting mixture was then concentrated in-vacuo and the residue purified via flash silica gel chromatography (Analogix IF-280, SF25-40 g column, gradient 90:10-10:90 heptane:EtOAc) to yield tert-butyl 3-(5-(3,4-dimethoxyphenylcarbamoyl)-1H-indol-2-yl) propyl(methyl)carbamate. $^1$H NMR (300 MHz, CDCl$_3$) δ 7.84 (s, 1H), 7.65 (d, J=8.4 Hz, 1H), 7.57 (s, 1H), 7.46 (d, J=8.0 Hz, 1H), 7.00 (d, J=8.6 Hz, 1H), 6.85 (d, J=8.6 Hz, 1H), 6.32 (s, 1H), 3.93 (s, 3H), 3.89 (s, 3H), 3.31-3.41 (m, 2H), 2.89 (s, 3H), 2.66-2.77 (m, 2H), 1.83-1.94 (m, 2H), and 1.53 (s, 9H). MS (ES$^+$) 468 (M+1).

STEP E: 2-(3-Methylamino-propyl)-1H-indole-5-carboxylic acid (3,4-dimethoxy-phenyl)-amide A 250 round bottom flask was charged with tert-butyl 3-(5-(3,4-dimethoxyphenylcarbamoyl)-1H-indol-2-yl)propyl(methyl)carbamate (2.75 g, 5.88 mmol), dichloromethane (32 mL), and 1M hydrochloric acid in diethyl ether (32 mL) and the resulting mixture stirred for 2.5 h. The resulting mixture was then concentrated in vacuo, the residue triturated with diethyl ether, and placed under high vacuum to yield 2-(3-methylamino-propyl)-1H-indole-5-carboxylic acid (3,4-dimethoxy-phenyl)-amide. MS (ES$^+$) 368 (M+1); HPLC: Kromasil C18 column (50×2 mm; 3.5µ), gradient 10-90% (MeCN+0.16% TFA) in (water+0.2% TFA) over 4 min, $t_R$=2.72 min.

STEP F: [1-({3-[5-(3,4-Dimethoxy-phenylcarbamoyl)-1H-indol-2-yl]propyl}-methyl-carbamoyl)-2-thiophen-2-yl-ethyl]-(S)-carbamic acid tert-butyl ester A 250 mL round bottom flask was charged with 2-(3-methylamino-propyl)-1H-indole-5-carboxylic acid (3,4-dimethoxy-phenyl)-amide (2.30 g, 5.70 mmol), 1-hydroxybenzotriazole hydrate (780 mg, 0.553 mmol), N-(3-dimethylaminopropyl)-N'-ethylcarbodiimide hydrochloride (1.65 g, 8.61 mmol), and dichlormethane (30 mL). Triethylamine (2.6 mL, 18.7 mmol) was added and the resulting mixture stirred at room temperature for 20 minutes. (S)-2-(tert-butoxycarbonylamino)-3-(thiophen-2-yl)propanoic acid (1.6 g, 5.90 mmol) was added and the resulting mixture was stirred at room temperature for 24 h. The resulting mixture was then concentrated in vacuo and the residue purified via flash silica gel chromatography (Analogix IF-280, SF25-40 g column, gradient 90:10-5:95 heptane:EtOAc) to yield [1-({3-[5-(3,4-dimethoxy-phenylcarbamoyl)-1H-indol-2-yl]-propyl}-methyl-carbamoyl)-2-thiophen-2-yl-ethyl]-(S)-carbamic acid tert-butyl ester. $^1$H NMR (300 MHz, CDCl$_3$) δ 7.85 (s, 1H), 7.66 (d, J=8.4 Hz, 1H), 7.58 (s, 1H), 7.47 (d, J=8.0 Hz, 1H), 7.17 (d, J=8.6 Hz, 1H), 6.90 (d, J=8.6 Hz, 1H), 6.73-6.87 (m, 3H), 6.30 (s, 1H), 3.94 (s, 3H), 3.89 (s, 3H), 3.78-3.87 (m, 1H), 3.30-3.43 (m, 2H), 2.93 (s, 3H), 2.61-2.76 (m, 2H), 1.81-1.93 (m, 2H), and 1.43 (s, 9H). MS (ES$^+$) 621 (M+1).

STEP G: (S)-2-(3-(2-amino-N-methyl-3-(thiophen-2-yl)propanamido)propyl)-N-(3,4-dimethoxyphenyl)-1H-indole-5-carboxamide A 50 mL round bottom flask was charged with [1-({3-[5-(3,4-dimethoxy-phenylcarbamoyl)-1H-indol-2-yl]-propyl}-methyl-carbamoyl)-2-thiophen-2-yl-ethyl]-(S)-carbamic acid tert-butyl ester (3.26 g, 2.52 mmol) and dichloromethane (36 mL). 1M Hydrochloric acid in diethyl ether (26 mL) was added and the resulting mixture stirred at room temperature for 2.5 h. The resulting mixture was then concentrated in vacuo to yield (S)-2-(3-(2-amino-N-methyl-3-(thiophen-2-yl)propanamido)propyl)-N-(3,4-dimethoxyphenyl)-1H-indole-5-carboxamide. $^1$H NMR (300 MHz, DMSO-d$_6$) δ 7.66-7.80 (m, 1H), 7.54 (s, 1H), 7.35-7.46 (m, 3H), 6.84-7.21 (m, 4H), 6.31 (s, 1H), 3.86-3.97 (m, 1H), 3.76 (s, 3H), 3.74 (s, 3H), 3.22-3.52 (m, 4H), 2.82 (s, 3H), 2.58-2.70 (m, 2H), and 1.79-1.89 (m, 2H); MS (ES$^+$) 521 (M+1); Anal. Calcd for C$_{28}$H$_{32}$N$_4$O$_4$S.1.25HCl.0.9; H$_2$O: C, 57.74; H, 6.17; N, 9.35; Cl, 7.56; H$_2$O, 2.72. Found: C, 57.65; H, 6.07; N, 9.62; Cl, 7.61; H$_2$O, 2.78.

Representative compounds of the present invention, listed in Table 9 below with their corresponding measured MS (ES$^+$) (M+1) mass spec numbers, were similarly prepared according to the procedures described in Example 8 above, by selecting and substituting suitably substituted reagent.

TABLE 9

Representative Compounds of Formula (I)

| ID No. | MH$^+$ |
|---|---|
| 107 | 453 |
| 118 | 535 |

EXAMPLE 9

(S)—N-(2-(1H-benzo[d]imidazol-2-yl)ethyl)-2-amino-3-(thiophen-2-yl)propanamide (Compound #37)

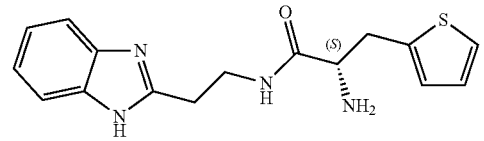

STEP A: {1-[2-(1H-Benzoimidazol-2-yl)-ethylcarbamoyl]-2-thiophen-2-yl-ethyl}-(S)-carbamic acid tert-butyl ester A 50 mL round bottom flask was charged with (S)-2-(tert-butoxycarbonylamino)-3-(thiophen-2-yl)propanoic acid (300 mg, 1.10 mmol), 1-hydroxybenzotriazole hydrate (75 mg, 0.55 mmol), O-benzotriazole-N,N,N', N'-tetramethyl-uronium-hexafluorophosphate (500 mg, 1.33 mmol), and dimethylformamide (5.0 mL). Triethylamine (0.77 mL, 0.55 mmol) and 2-(1H-benzo[d]imidazol-2-yl)ethanamine (388.2 mg, 1.66 mmol) were added and the resulting mixture stirred at room temperature for 22 h. The resulting mixture was then concentrated in vacuo and the residue purified via flash silica gel chromatography (ISCO, SF25-40 g column, gradient 90:10-75:25 Heptane:EtOAc) to yield {1-[2-(1H-benzoimidazol-2-yl)-ethylcarbamoyl]-2-thiophen-2-yl-ethyl}-(S)-carbamic acid tert-butyl ester. $^1$H NMR (300 MHz, CDCl$_3$) 6.7.73-7.69 (m, 2H), 7.29-7.37 (m, 2H), 7.54-7.33 (m, 4H), 7.11 (d, J=8.2 Hz, 1H), 6.82-6.88 (m, 2H), 5.32 (t, J=3.71 Hz, 1H), 4.33 (m, 1H), 3.78-3.97 (s, 2H), 3.45-3.35 (m, 2H), 3.15-2.91 (m, 4H) and 1.41-1.21 (m, 9H); MS (ES$^+$) 415 (M+1).

STEP B: (S)—N-(2-(1H-benzo[d]imidazol-2-yl)ethyl)-2-amino-3-(thiophen-2-yl)propanamide A 50 mL round bottom flask was charged with {1-[2-(1H-benzoimidazol-2-yl)-ethylcarbamoyl]-2-thiophen-2-yl-ethyl}-(S)-carbamic acid tert-butyl ester (100.0 mg, 0.24 mmol) and dichloromethane (4 mL). 1M trifluoroacetitic acid (1 mL) was added and the resulting mixture was stirred at room temperature for 3 h. The resulting mixture was then concentrated in vacuo and the residue (an oil) was purified on a Gilson HPLC with a reversed phase Kromasil column (10u, 100 Å C18, column length 250×50 mm, gradient 0-60 MeCN: H₂O). The resulting solid was taken up in dichloromethane and treated with 1M hydrochloric acid in diethyl ether. The resulting mixture was concentrated in vacuo and this procedure was repeated two more times to yield (S)—N-(2-(1H-benzo[d]imidazol-2-yl)ethyl)-2-amino-3-(thiophen-2-yl)propanamide. ¹H NMR (300 MHz, MeOH-d4) δ 7.89-7.75 (m, 2H), 7.69-7.58 (d, 2H), 7.32-7.21 (d, J=8.2 Hz, 1H), 6.99-6.91 (m, 2H), 4.03 (t, J=3.71 Hz, 1H), 3.75-3.89 (m, 2H), 3.59-3.3.31 (m, 4H), 3.04 (s, 1H), 2.64-2.79 (m, 2H), 2.80 (s, 1H); MS (ES⁺) 315 (M+1).

Representative compounds of the present invention, listed in Table 10 below with their corresponding measured MS (ES⁺) (M+1) mass spec numbers, were similarly prepared according to the procedures described in Example 9 above, by selecting and substituting suitably substituted reagent.

TABLE 10

Representative Compounds of Formula (I)

| ID No. | MH⁺ |
|---|---|
| 37 | 315 |
| 38 | 247 |
| 39 | 261 |

EXAMPLE 10

(S)-2-amino-1-(4-(5-(3,4-dimethoxyphenyl)-1H-benzo[d]imidazol-2-yl)piperidin-1-yl)-3-(thiophen-2-yl)propan-1-one (Compound #18)

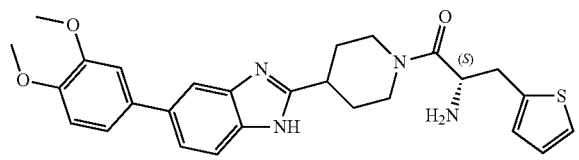

STEP A: (S)-tert-Butyl 1-(4-(5-bromo-1H-benzo[d]imidazol-2-yl)piperidin-1-yl)-1-oxo-3-(thiophen-2-yl)propan-2-ylcarbamate A 250 mL round bottom flask was charged with (S)-2-(tert-butoxycarbonylamino)-3-(thiophen-2-yl)propanoic acid (569.0 mg, 0.2.10 mmol), 1-hydroxybenzotriazole hydrate (142.0 mg, 1.05 mmol), O-Benzotriazole-1-yl-N,N,N'N'-tetramethyluronium hexafluorophosphate (1025.0 mg, 2.73 mmol) and dimethylformamide (7.0 mL). Triethylamine (1.17 mL, 8.39 mmol) and 5-bromo-2-piperidin-4-yl-1H-benzoimidazole hydrochloride salt (730.0 mg, 2.306 mmol) were added and the resulting mixture stirred at room temperature for 22 h. The resulting mixture was then concentrate in vacuo and the residue purified via reverse phase HPLC ("RPHPLC") (gradient 20-90, MeCN-Water) to yield (S)-tert-butyl 1-(4-(5-bromo-1H-benzo[d]imidazol-2-yl)piperidin-1-yl)-1-oxo-3-(thiophen-2-yl)propan-2-ylcarbamate as its corresponding trifluoroacetate salt. ¹H NMR (300 MHz, DMSO-D6) δ 7.92 (s, 1H), 7.65 (m, 1H), 7.54 (m, 1H), 7.32-7.25 (m, 2H), 6.96-6.91 (m, 2H), 4.65 (m, 1H), 4.42- 4.15 (m, 2H), 3.31-3.11 (m, 4H), 2.99 (m, 1H), 2.15-2.61 (m, 2H), and 1.73 (m, 2H), 1.43 (s, 9H); MS (ES+) 648 (M+1).

STEP B: (2-{4-[5-(3,4-Dimethoxy-phenyl)-1H-benzoimidazol-2-yl]-piperidin-1-yl}-2-oxo-1-thiophen-2-ylmethyl-ethyl)-(S)-carbamic acid tert-butyl ester A 10 mL sealed tube was charged with (S)-tert-butyl 1-(4-(5-bromo-1H-benzo[d]imidazol-2-yl)piperidin-1-yl)-1-oxo-3-(thiophen-2-yl)propan-2-ylcarbamate (200 mg, 0.31 mmol), 3,4-dimethoxyphenylboronic acid (67.5 mg, 0.37 mmol), 1,1'-bis(di-t-butylphosphino)ferrocene palladium dichloride (10.07 mg, 0.015 mmol), 10% aqueous sodium carbonate (0.82 mL), and 1,4-dioxane (2 mL). The vessel was then flushed with argon and sealed. The resulting mixture was stirred at 100° C. for 24 h, then diluted with dichloromethane (300 mL) and washed with water (10 mL). The organic layer was dried with Na₂SO₄, filtered, concentrated and the residue purified by RPHPLC (15-90, gradient, MeCN-water), dried in vacuo to yield (2-{4-[5-(3,4-dimethoxy-phenyl)-1H-benzoimidazol-2-yl]-piperidin-1-yl}-2-oxo-1-thiophen-2-ylmethyl-ethyl)-(S)-carbamic acid tert-butyl ester as its corresponding trifluoroacetate salt. MS (ES⁺) 591 (M+1).

STEP C: (S)-2-amino-1-(4-(5-(3,4-dimethoxyphenyl)-1H-benzo[d]imidazol-2-yl)piperidin-1-yl)-3-(thiophen-2-yl)propan-1-one A 25 mL round bottom flask was charged with (2-{4-[5-(3,4-dimethoxy-phenyl)-1H-benzoimidazol-2-yl]-piperidin-1-yl}-2-oxo-1-thiophen-2-ylmethyl-ethyl)-(S)-carbamic acid tert-butyl ester as trifluoroacetate salt (230 mg, 0.326 mmol) and 1,4-dioxane (1.5 mL). 4M Hydrochloric acid in 1,4-dioxane (1.63 mL) was added and the resulting mixture was stirred at room temperature for 3 h. The resulting mixture was then concentrated in vacuo to yield (S)-2-amino-1-(4-(5-(3,4-dimethoxyphenyl)-1H-benzo[d]imidazol-2-yl)piperidin-1-yl)-3-(thiophen-2-yl)propan-1-one. ¹H NMR (300 MHz, DMSO-d₆) δ 8.45 (m, 2H), 7.91-7.85 (m, 2H), 7.61-7.58 (d, J=8.4 Hz, 1H), 7.3-7.2 (m, 2H), 6.85-7.0 (m, 3H), 4.75 (m, 1H), 4.52-4.13 (m, 2H), 3.96-3.84 (s, 6H), 3.43-3.33 (m, 4H), 2.96 (m, 1H), 2.24-1.86 (m, 4H); MS (ES⁺) 491 (M+1).g Representative compounds of the present invention, listed in Table 11 below with their corresponding measured MS (ES⁺) (M+1) mass spec numbers, were similarly prepared according to the procedures described in Example 9 above, by selecting and substituting suitably substituted reagent.

TABLE 11

Representative Compounds of Formula (I)

| ID No. | MH⁺ |
|---|---|
| 16 | 434 |
| 19 | 474 |

EXAMPLE 11

(S)-2-amino-N-(3-(5-(3,4-dimethoxyphenoxy)-1H-indol-2-yl)propyl)butanamide (Compound #99)

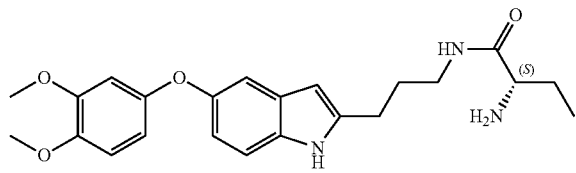

STEP A: (1-Pent-4-ynylcarbamoyl-propyl)-(S)-carbamic acid tert-butyl ester

A 500 mL round bottom flask was charged with (S)-2-(tert-butoxycarbonylamino)butanoic acid (5.0 g, 0.025 mol), 1-hydroxybenzotriazole hydrate (4.5 g, 0.033 mol), N-(3-dimethylaminopropyl)-N'-ethylcarbodiimide hydrochloride (6.4 g, 0.033 mol), 4-(dimethylamino)pyridine (0.02 g, 0.163 mmol), and dimethylformamide (95 mL). Triethylamine (10.6 mL, 0.076 mol) and pent-4-yn-1-amine (2.7 g, 0.033 mol) were added and the resulting mixture stirred at room temperature for 22 h. The resulting mixture was then concentrated in vacuo and the residue purified via flash silica gel chromatography (Analogix IF-280, SF65-400 g column, gradient 90:10-40:60 Heptane:EtOAc) to yield (1-pent-4-ynylcarbamoyl-propyl)-(S)-carbamic acid tert-butyl ester. $^1$H NMR (300 MHz, CDCl$_3$) δ 3.93-4.00 (m, 1H), 3.36-3.42 (m, 2H), 2.22-2.28 (m, 2H), 2.00 (s, 1H), 1.83-1.92 (m, 1H), 1.70-1.80 (m, 2H), 1.57-1.67 (m, 1H), 1.45 (s, 9H), and 0.94 (t, J=7.4 Hz, 3H).

STEP B: {1-[5-(2-Amino-5-bromo-phenyl)-pent-4-ynylcarbamoyl]-propyl}-(S)-carbamic acid tert-butyl ester A 50 mL round bottom flask was charged with (1-pent-4-ynylcarbamoyl-propyl)-(S)-carbamic acid tert-butyl ester (2.24 g, 8.36 mmol), 4-bromo-2-iodoaniline (2.38 g, 8.59 mmol), copper iodide (0.21 g, 1.10 mmol), palladium tetrakistriphenylphosphine (1.12 g, 0.97 mmol), and diethylamine (300 mL) and the resulting mixture stirred at room temperature for 4 h. The resulting mixture was then concentrated in vacuo and the residue purified via flash silica gel chromatography (Analogix IF-280, SF40-400 g column, gradient 90:10-10:90 Heptane:EtOAc) to yield {1-[5-(2-{1-[5-(2-amino-5-bromo-phenyl)-pent-4-ynylcarbamoyl]-propyl}-(S)-carbamic acid tert-butyl ester mino-5-bromo-phenyl)-pent-4-ynylcarbamoyl]-propyl}-(S)-carbamic acid tert-butyl ester. $^1$H NMR (300 MHz, CDCl$_3$) δ 7.94 (s, 1H), 7.76 (d, J=6.5 Hz, 1H), 6.64 (d, J=8.5 Hz, 1H), 3.91-4.09 (m, 1H), 3.85 (s, 3H), 3.47-3.52 (m, 2H), 2.52 (t, J=6.8 Hz, 2H), 1.75-1.92 (m, 3H), 1.60-1.69 (m, 1H), 1.44 (s, 9H), and 0.94 (t, J=7.4 Hz, 3H); MS (ES$^+$) 439 (M+1).

STEP C: (1-{3-[5-(3,4-Dimethoxy-phenoxy)-1H-indol-2-yl]-propylcarbamoyl}-propyl)-(S)-carbamic acid tert-butyl ester A 100 mL sealed tube was charged with {1-[5-(2-amino-5-bromo-phenyl)-pent-4-ynylcarbamoyl]-propyl}-(S)-carbamic acid tert-butyl ester (0.5 g, 1.22 mmol), 3,4-dimethoxyphenylboronic acid (0.28 g, 1.83 mmol), cesium carbonate (0.8 g, 2.44 mmol), N,N-dimethylglycene hydrochloride salt (0.15 g, 1.1 mmol), copper iodide (0.07 g, 0.36 mmol), 1,4-dioxane (2.5 mL). The vessel was then flushed with argon and sealed and the resulting mixture stirred at 120° C. for 24 h. The resulting mixture was then washed with water (25 mL) and extracted with ethyl acetate. The organic layer was dried with Na$_2$SO$_4$, filtered, and concentrated in vacuo. The resulting residue was purified by RPHPLC (gradient 35-90, acetonitrile-water) to yield (1-{3-[5-(3,4-dimethoxy-phenoxy)-1H-indol-2-yl]-propylcarbamoyl}-propyl)-(S)-carbamic acid tert-butyl ester. $^1$H NMR (300 MHz, CDCl$_3$) δ 9.51 (s, 1H), 7.12 (s, 1H), 6.94-6.82 (m, 2H), 6.75-6.79 (m, 1H), 6.67-6.63 (d, J=3.0 Hz, 1H), 6.15 (t, J=6.0 Hz, 1H), 6.05 (s, 1H), 4.06 (m, 1H), 3.93 (s, 6H), 3.63-3.31 (m, 2H), 2.74 (m, 2H), 1.81-1.67 (m, 4H), and 1.49 (s, 9H), 0.96 (t, J=7.0 Hz, 3H); MS (ES$^+$) 512 (M+1).

STEP D

A 50 mL round bottom flask was charged with (1-{3-[5-(3,4-dimethoxy-phenoxy)-1H-indol-2-yl]-propylcarbamoyl}-propyl)-(S)-carbamic acid tert-butyl ester (110 mg, 0.21 mmol) and dichloromethane (3 mL). 1M Hydrochloric acid in diethyl ether (3 mL) was added and the resulting mixture stirred at room temperature for 3 h. The resulting mixture was then concentrated in vacuo to yield (S)-2-amino-N-(3-(5-(3,4-dimethoxyphenoxy)-1H-indol-2-yl)propyl)butanamide. $^1$H NMR (300 MHz, DMSO-d$_6$) 611 (s, 1H), 8.15 (br s, 1H), 7.29-7.25 (d, J=9 Hz, 1H), 6.92 (m, 1H), 6.81 (d, J=8 Hz, 1H), 6.72 (m, 2H), 6.85 (m, 1H), 6.15 (s, 1H), 3.73 (s, 6H), 3.65 (m, 1H), 3.37-3.15 (m, 2H), 2.75 (t, J=7 Hz, 2H), 1.91-1.62 (m, 4H), and 0.97 (t, J=7.2 Hz, 3H); MS (ES$^+$) 412 (M+1).

Compound #98 was similarly prepared according to the procedure described in Example 11 above, with a measured MS (ES$^+$) of 352 (M+1).

BIOLOGICAL EXAMPLE 1

DPP-1 Inhibiiton Assay (In Vitro)

Test compounds were assessed for DPP-1 (Cathepsin C) inhibitory activity using a fluorogenic substrate, GR-AMC (Glycine-Arginine-amino-4-methylcoumarin, Bachem, I-1215). The amount of amino-methylcoumarin released is proportional to the DPP-1 activity, and the reaction is monitored kinetically with a Molecular Devices plate reader using black 96-well plates.

All compounds were tested under room temperature conditions. The assay buffer consisted of 50 mM HEPES, pH 7.0, 100 mM NaCl, 2 mM glutathione (GSH), and 0.002% TWEEN 20. GSH and TWEEN 20 were added to the buffer fresh daily. Just prior to use, an in-house preparation of recombinant human DPP-1 (240 μM stock, MW 49.6 kD) was diluted 600-fold in assay buffer containing fresh 2 mM dithiothreitol (DTT) to activate the enzyme, then diluted into assay buffer (without DTT) 133-fold for a DPP-1 working solution of 3 nM. Test compounds were diluted in DMSO for 20× their final assay concentrations.

Additions to a 96-well black Costar 3915 plates were as follows: 90 μL of 11 μM GR-AMC, 5 μL test compound (followed by mixing), and 5 μL 3 nM DPP1 to start the reaction. Fluorescent reactions were monitored kinetically at 360 nm excitation, 440 nm emission on a Molecular Devices Spectramax XPS reader. The Softmax Pro software of the reader determined the initial velocity of the selected data (the first 3-5 minutes of the reaction), and the best linear regression fit of the initial kinetic data. Final assay conditions were 0.15 nM DPP-1, 10 uM GR-AMC, 50 mM HEPES, pH 7.0, 100 mM NaCl, 2 mM GSH, 0.002% TWEEN 20, 1 uM DTT, 5.0% DMSO. Initial velocity rates were plotted vs. test compound concentration by use of a four-parameter logistics equation (nonlinear regression, sigmoidal dose-response (variable slope), with fixed Hill (1.0) using GraphPad Prism® software for determination of DPP-1 $IC_{50}$. Within-run assay coefficient of variation (CV) was generally <10%; between-run CV <20%.

Representative compounds of the present invention were tested according to the procedure as described above, with results as listed in Table 12, below. Where a compound was tested according to the above procedure multiple times, the average value is listed in the Table below.

TABLE 12

DPP-1 Inhibition

| ID No | $IC_{50}$ (µM) |
|---|---|
| 1 | 1.20 |
| 2 | 0.094 |
| 3 | 0.27 |
| 4 | 0.33 |
| 5 | 0.30 |
| 6 | 0.26 |
| 7 | 0.14 |
| 8 | 0.46 |
| 9 | 3.70 |
| 10 | ~12.00 |
| 11 | ~12.00 |
| 12 | 14.00 |
| 13 | 0.85 |
| 14 | 3.37 |
| 15 | 2.20 |
| 16 | 0.71 |
| 17 | 0.16 |
| 18 | 0.21 |
| 19 | 0.24 |
| 20 | 0.20 |
| 21 | 0.54 |
| 22 | 18.00 |
| 23 | 0.11 |
| 24 | 5.80 |
| 25 | 0.25 |
| 26 | 0.23 |
| 27 | 0.59 |
| 28 | >20[a] |
| 29 | >20[a] |
| 30 | >20[a] |
| 35 | 1.30 |
| 36 | >10[a] |
| 37 | 4.25 |
| 38 | 6.50 |
| 39 | 43.00 |
| 40 | 2.90 |
| 41 | 6.30 |
| 42 | 3.30 |
| 43 | 14.00 |
| 44 | 10.00 |
| 45 | 9.60 |
| 46 | 41.99 |
| 47 | 53.00 |
| 48 | 6.30 |
| 49 | 19.00 |
| 50 | 0.24 |
| 51 | 4.10 |
| 52 | 4.00 |
| 53 | 7.40 |
| 54 | 0.85 |
| 55 | 0.22 |
| 56 | 1.10 |
| 57 | 0.70 |
| 58 | 0.73 |
| 59 | 1.40 |
| 61 | 4.30 |

TABLE 12-continued

DPP-1 Inhibition

| ID No | $IC_{50}$ (µM) |
|---|---|
| 62 | 2.80 |
| 63 | 2.50 |
| 64 | 0.35 |
| 65 | 0.48 |
| 66 | 0.91 |
| 67 | 0.20 |
| 68 | 0.71 |
| 69 | 0.56 |
| 70 | 0.89 |
| 71 | 2.60 |
| 72 | 2.40 |
| 73 | 1.80 |
| 74 | >10[a] |
| 75 | 1.10 |
| 76 | 0.82 |
| 77 | 0.35 |
| 78 | 0.91 |
| 79 | 1.30 |
| 80 | 0.68 |
| 81 | 0.79 |
| 82 | 0.53 |
| 83 | 0.56 |
| 84 | 1.00 |
| 85 | 2.40 |
| 86 | 1.00 |
| 87 | 2.60 |
| 88 | 1.00 |
| 89 | 1.20 |
| 90 | 0.90 |
| 91 | 0.80 |
| 92 | 0.35 |
| 93 | 0.92 |
| 94 | 1.50 |
| 95 | 0.43 |
| 96 | 0.37 |
| 97 | 0.024 |
| 98 | 0.48 |
| 99 | 0.42 |
| 100 | 0.52 |
| 101 | 0.79 |
| 102 | 0.71 |
| 103 | 0.39 |
| 104 | 0.34 |
| 105 | 0.86 |
| 106 | 0.082 |
| 107 | 9.00 |
| 108 | >10[a] |
| 109 | 0.76 |
| 110 | >10[a] |
| 111 | 0.69 |
| 112 | 0.52 |
| 113 | 0.70 |
| 114 | 0.67 |
| 115 | >10[a] |
| 116 | 2.00 |
| 117 | 0.081 |
| 118 | 0.37 |

[a]For these compound, the number of different concentrations tested was not sufficient to calculate an $IC_{50}$ value beyond a determination that it was greater than about 10 µM or greater than 20 µM, as noted.

SOLID, ORAL FORMULATION

Prophetic Example

As a specific embodiment of an oral composition, 100 mg of the Compound #2, prepared as in Example 6, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations

What is claimed:

1. A compound of formula (I)

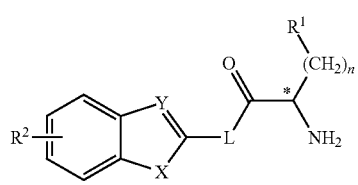

wherein
R$^1$ is selected from the group consisting of C$_{1-2}$alkyl, —C(O)—NH$_2$, C$_{3-6}$cycloalkyl, phenyl and 5 to 6 membered heteroaryl; wherein the heteroaryl is optionally substituted with one or more substituents independently selected from halogen and C$_{1-4}$alkyl;
n is an integer from 0 to 1;
L is selected from the group consisting of

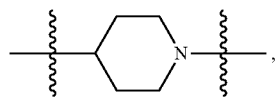 [SMILES: *C1CCN(*)CC1]

—CH$_2$CH$_2$—NR$^A$— and —CH$_2$CH$_2$CH$_2$—NR$^A$—;
wherein R$^A$ is selected from the group consisting of hydrogen, methyl and ethyl;
Y is selected from the group consisting of N and CH;
X is selected from the group consisting of N(R$^B$), O and S; wherein R$^B$ is selected from the group consisting of hydrogen and C$_{1-2}$alkyl;
R$^2$ is selected from the group consisting of hydrogen, halogen, nitro, —CO$_2$H, —C(O)—NR$^C$R$^D$, -Q, —O-Q and —C(O)—NH-Q;
wherein R$^C$ and R$^D$ are each independently selected from the group consisting of hydrogen and C$_{1-4}$alkyl; alternatively, R$^C$ and R$^D$ are taken together with the nitrogen atom to which they are bound to form a ring structure selected from the group consisting of piperidin-1-yl, piperazin-1-yl, pyrrolidin-1-yl, morpholin-4-yl, 1,2,3,4-tetrahydroquinolin-1-yl and 1,2,3,4-tetrahydro-isoquinolin-2-yl;
wherein Q is selected from the group consisting of aryl, aralkyl, heterocyclyl, benzo[d][1,3]dioxolyl and 2,3-dihydro-benzo[b][1,4]dioxinyl;
wherein the aryl or heterocyclyl, whether alone or as part of a substituent group, is optionally substituted with one or more substituents independently selected from the group consisting of halogen, cyano, C$_{1-4}$alkyl, halogenated C$_{1-4}$alkyl, C$_{1-4}$alkoxy, halogenated C$_{1-4}$alkoxy, —CO$_2$H, —C(O)—NR$^E$R$^F$, SO$_2$—NR$^E$R$^F$ and phenyl; wherein R$^E$ and R$^F$ are each independently selected from the group consisting of hydrogen and C$_{1-4}$alkyl;
and wherein the heterocyclyl contains one or more S heteroatoms, said heterocyclyl may be further optionally substituted on said one or more S heteroatoms with one to two oxo groups;
or a pharmaceutically acceptable salt thereof.

2. A compound as in claim 1, wherein
R$^1$ is selected from the group consisting of C$_{1-2}$alkyl, —C(O)—NH$_2$, C$_{3-6}$cycloalkyl, phenyl and 5 to 6 membered heteroaryl; wherein the 5 to 6 membered heteroaryl is optionally substituted with one to two substituent selected from the group consisting of halogen and C$_{1-4}$alkyl;
n is an integer from 0 to 1;
L is selected from the group consisting of

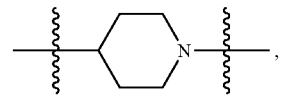

—CH$_2$CH$_2$—N(R$^A$)— and —CH$_2$CH$_2$CH$_2$—N(R$^A$)—;
wherein R$^A$ is selected from the group consisting of hydrogen, methyl and ethyl;
Y is selected from the group consisting of N and CH;
X is selected from the group consisting of N(R$^B$), O and S; wherein R$^B$ is selected from the group consisting of hydrogen and C$_{1-2}$alkyl;
R$^2$ is selected from the group consisting of hydrogen, halogen, nitro, —CO$_2$H, —C(O)—NR$^C$R$^D$, phenyl, —O-phenyl, heterocyclyl, and —C(O)—NH-Q;
wherein R$^C$ and R$^D$ are each independently selected from the group consisting of hydrogen and C$_{1-4}$alkyl; alternatively, R$^C$ and R$^D$ are taken together with the nitrogen atom to which they are bound to form a ring structure selected from the group consisting of piperidin-1-yl, pyrrolidin-1-yl, 1,2,3,4-tetrahydroquinolin-1-yl and 1,2,3,4-tetrahydro-isoquinolin-2-yl;
wherein Q is selected from the group consisting of aryl, aralkyl, heterocyclyl, benzo[d][1,3]dioxolyl and 2,3-dihydro-benzo[b][1,4]dioxinyl;
wherein the aryl or heterocyclyl, whether alone or as part of a substituent group, is optionally substituted with one to two substituents independently selected from the group consisting of halogen, cyano, C$_{1-4}$alkyl, fluorinated C$_{1-4}$alkyl, C$_{1-4}$alkoxy, fluorinated C$_{1-4}$alkoxy, —CO$_2$H, —C(O)NR$^E$R$^F$, —SO$_2$—NR$^E$R$^F$ and phenyl; wherein R$^E$ and R$^F$ are each independently selected from the group consisting of hydrogen and C$_{1-2}$alkyl;
and wherein the heterocyclyl contains one or more S heteroatoms, said heterocyclyl may be further optionally substituted on said one or more S heteroatoms with one to two oxo groups;
or a pharmaceutically acceptable salt thereof.

3. A compound as in claim 2, wherein
R$^1$ is selected from the group consisting of C$_{1-2}$alkyl, —C(O)—NH$_2$, C$_{4-6}$cycloalkyl and 5 to 6 membered heteroaryl; wherein the 5 to 6 membered heteroaryl is optionally substituted with a substituent selected from the group consisting of halogen and C$_{1-4}$alkyl;
n is an integer from 0 to 1;
L is selected from the group consisting of

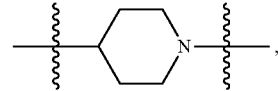 [SMILES: *C1CCN(*)CC1]

—CH$_2$CH$_2$—N(R$^A$)— and —CH$_2$CH$_2$CH$_2$—N(R$^A$)—;
wherein R$^A$ is selected from the group consisting of hydrogen, methyl and ethyl;
Y is selected from the group consisting of N and CH;

X is selected from the group consisting of N(R$^B$) and O;
wherein R$^B$ is selected from the group consisting of hydrogen and C$_{1-2}$alkyl;

R$^2$ is selected from the group consisting of hydrogen, halogen, nitro, carboxy, phenyl, —O-phenyl, —C(O)—NR$^C$R$^D$ and —C(O)—NH-Q;

wherein R$^C$ and R$^D$ are each independently selected from the group consisting of hydrogen and C$_{1-2}$alkyl; alternatively, R$^C$ and R$^D$ are taken together with the nitrogen atom to which they are bound to form a ring structure selected from the group consisting of 1,2,3,4-tetrahydro-quinolin1-yl and 1,2,3,4-tetrahydroisoquinolin-2-yl;

wherein Q is selected from the group consisting of phenyl, naphthyl, —C$_{1-2}$alkyl-phenyl, heterocyclyl, benzo[d][1,3]dioxolyl and 2,3-dihydro-benzo[b][1,4]dioxinyl;

wherein the phenyl or heterocyclyl, whether alone or as part of a substituent group, is optionally substituted with one to two substituents independently selected from the group consisting of halogen, cyano, C$_{1-4}$alkyl, fluorinated C$_{1-2}$alkyl, C$_{1-4}$alkoxy, fluorinated C$_{1-2}$alkoxy, —CO$_2$H, —C(O)NH$_2$, —SO$_2$—NH$_2$ and phenyl;

and wherein the heterocyclyl contains one or more S heteroatoms, said heterocyclyl may be further optionally substituted on said one or more S heteroatoms with one to two oxo groups;

or a pharmaceutically acceptable salt thereof.

4. A compound as in claim 3, wherein

R$^1$ is selected from the group consisting of ethyl, cyclobutyl, thien-2-yl, thien-3-yl, 2-bromo-thien-2-yl, 5-chloro-thien-2-yl, thiazol-2-yl, 4-methyl-thiazol-2-yl, pyrazol-1-yl, fur-2-yl, 1-methyl-imidazol-4-yl and amino-carbonyl;

n is an integer from 0 to 1;

L is selected from the group consisting of

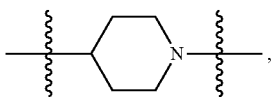

—CH$_2$CH$_2$—NH—, —CH$_2$CH$_2$CH$_2$—NH—, —CH$_2$CH$_2$CH$_2$—N(CH$_3$)— and —CH$_2$CH$_2$CH$_2$—N(CH$_2$CH$_3$)—;

Y is selected from the group consisting of CH and N;

X is selected from the group consisting of NH, N(CH$_3$) and O;

provided that when X is O, then Y is CH;

R$^2$ is selected from the group consisting of hydrogen, 5-bromo, 5-(carboxy), 5-(nitro), 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(2-(aminocarbonyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 6-(diethylamino-carbonyl), 5-(phenyl-amino-carbonyl), 5-(3-chlorophenyl-amino-carbonyl), 5-(4-chlorophenyl-amino-carbonyl), 5-(2-fluorophenyl-amino-carbonyl), 5-(3-fluorophenyl-amino-carbonyl), 5-(4-fluorophenyl-amino-carbonyl), 5-(3-methylphenyl-amino-carbonyl), 5-(4-methylphenyl-amino-carbonyl), 5-(2-isopropylphenyl-amino-carbonyl), 5-(4-isopropylphenyl-amino-carbonyl), 5-(4-t-butylphenyl-amino-carbonyl), 5-(2-methoxyphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4-dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(3,5-dimethoxyphenyl-amino-carbonyl), 5-(naphth-1-yl-amino-carbonyl), 5-(benzyl-amino-carbonyl), 5-([1,2,4]triazol-3-yl-amino-carbonyl), 5-(pyrid-3-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(benzimidazol-4-yl-amino-carbonyl), 5-(benzimidazol-5-yl-amino-carbonyl), 5-(1-methyl-benzimidazol-4-yl-amino-carbonyl), 5-(pyrazol-3-yl-amino-carbonyl), 5-(5-phenyl-pyrazol-3-yl-amino-carbonyl), 5-(1H-pyrazolo[3,4-d]pyrimidin-4-yl-amino-carbonyl), 5-(1,1-dioxo-benzothiophen-6-yl-amino-carbonyl), 5-(1,2,3,4-tetrahydro-quinolin-1-yl-amino-carbonyl), 5-(1,2,3,4-tetrahydro-quinolin-1-yl-carbonyl), 5-(1,2,3,4-tetrahydro-isoquinolin-2-yl-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl);

or a pharmaceutically acceptable salt thereof.

5. A compound as in claim 4, wherein

R$^1$ is selected from the group consisting of ethyl, thien-2-yl, thiazol-2-yl, fur-2-yl and 1-methyl-imidazol-4-yl;

n is an integer from 0 to 1;

L is selected from the group consisting of

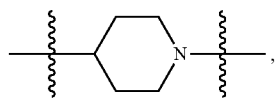

—CH$_2$CH$_2$—NH—, —CH$_2$CH$_2$CH$_2$—NH— and —CH$_2$CH$_2$CH$_2$—N(CH$_2$CH$_3$)—;

Y is selected from the group consisting of CH and N;

X is selected from the group consisting of NH and O;

provided that when X is O, then Y is CH;

R$^2$ is selected from the group consisting of hydrogen, 5-bromo, 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(2-(aminocarbonyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 5-(phenyl-amino-carbonyl), 5-(3-chlorophenyl-amino-carbonyl), 5-(4-chlorophenyl-amino-carbonyl), 5-(2-fluorophenyl-amino-carbonyl), 5-(3-fluorophenyl-amino-carbonyl), 5-(4-fluorophenyl-amino-carbonyl), 5-(3-methylphenyl-amino-carbonyl), 5-(4-methylphenyl-amino-carbonyl), 5-(2-isopropylphenyl-amino-carbonyl), 5-(4-isopropylphenyl-amino-carbonyl), 5-(4-t-butylphenyl-amino-carbonyl), 5-(2-methoxyphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4- dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(3,5-dimethoxyphenyl-amino-carbonyl), 5-(naphth-1-yl-amino-carbonyl), 5-(pyrid-3-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(benzimidazol-4-yl-amino-carbonyl), 5-(benzimidazol-5-yl-amino-carbonyl), 5-(1-methyl-benzimidazol-4-yl-amino-carbonyl), 5-(pyrazol-3-yl-amino-carbonyl), 5-(5-phenyl-pyrazol-3-yl-amino-carbonyl), 5-(1H-pyrazolo[3,4-d]pyrimidin-4-yl-amino-carbonyl), 5-(1,1-dioxo-benzothiophen-6-yl-amino-carbonyl), 5-(1,2,3,4-tetrahydro-quinolin-1-yl-amino-carbonyl), 5-(1,2,3,4-tetrahydro-quinolin-1-yl-carbonyl), 5-(1,2,3,4-tetrahydro-isoquinolin-2-yl-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl);

and wherein the starred stereo-center is present in an enantiomeric excess of the (S)-stereo-configuration;

or a pharmaceutically acceptable salt thereof.

6. A compound as in claim 4, wherein

R¹ is selected from the group consisting of ethyl, thien-2-yl, thiazol-2-yl and fur-2-yl;

n is an integer from 0 to 1;

L is selected from the group consisting of

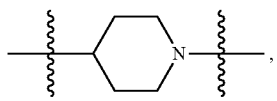

—CH₂CH₂CH₂—NH— and —CH₂CH₂CH₂—N(CH₂CH₃)—;

Y is selected from the group consisting of CH and N;

X is selected from the group consisting of NH and O;

provided that when X is O, then Y is CH;

R² is selected from the group consisting of 5-bromo, 5-(phenyl), 5-(4-fluorophenyl), 5-(4-methoxy-phenyl), 5-(3,4-dimethoxy-phenyl), 5-(3,5-dimethoxy-phenyl), 5-(3-cyano-phenyl), 5-(3-carboxy-phenyl), 5-(4-carboxy-phenyl), 5-(4-trifluoromethyl-phenyl), 5-(4-trifluoromethoxy-phenyl), 5-(3,5-di(trifluoromethyl)-phenyl), 5-(3-(aminocarbonyl)-phenyl), 5-(4-(aminocarbonyl)-phenyl), 5-(3-(aminosulfonyl)-phenyl), 5-(phenoxy), 5-(3,4-dimethoxy-phenoxy), 5-(3-chlorophenyl-amino-carbonyl), 5-(4-chlorophenyl-amino-carbonyl), 5-(3-fluorophenyl-amino-carbonyl), 5-(3-methylphenyl-amino-carbonyl), 5-(4-isopropylphenyl-amino-carbonyl), 5-(4-t-butylphenyl-amino-carbonyl), 5-(3-methoxyphenyl-amino-carbonyl), 5-(4-methoxyphenyl-amino-carbonyl), 5-(3,4-difluorophenyl-amino-carbonyl), 5-(3,4-dichlorophenyl-amino-carbonyl), 5-(3,4-dimethylphenyl-amino-carbonyl), 5-(2,6-dimethylphenyl-amino-carbonyl), 5-(3,4-dimethoxyphenyl-amino-carbonyl), 5-(naphth-1-yl-amino-carbonyl), 5-(quinolin-3-yl-amino-carbonyl), 5-(quinolin-5-yl-amino-carbonyl), 5-(quinolin-6-yl-amino-carbonyl), 5-(quinolin-8-yl-amino-carbonyl), 5-(isoquinolin-5-yl-amino-carbonyl), 5-(isoquinolin-8-yl-amino-carbonyl), 5-(benzothiazol-6-yl-amino-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl);

and wherein the starred stereo-center is present in an enantiomeric excess of the (S)-stereo-configuration;

or a pharmaceutically acceptable salt thereof.

7. A compound as in claim 4, wherein

R¹ is selected from the group consisting of ethyl, thien-2-yl and thiazol-2-yl;

n is an integer from 0 to 1;

L is selected from the group consisting of

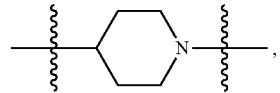

—CH₂CH₂CH₂—NH— and —CH₂CH₂CH₂—N(CH₂CH₃)—;

Y is selected from the group consisting of CH and N;

X is selected from the group consisting of NH and O;

provided that when X is O, then Y is CH;

R² is selected from the group consisting of 5-(4-methoxy-phenyl), 5-(3,4-dimethoxy-phenyl), 5-(3,5-dimethoxy-phenyl), 5-(3-cyano-phenyl), 5-(4-carboxy-phenyl), 5-(3-(aminocarbonyl)-phenyl), 5-(phenoxy), 5-(3,4-dimethoxy-phenoxy), 5-(3-methoxyphenyl-amino-carbonyl), 5-(4-methoxyphenyl-amino-carbonyl), 5-(2,6-dimethylphenyl-amino-carbonyl), 5-(3,4-dimethoxyphenyl-amino-carbonyl), 5-(quinolin-3-yl-amino-carbonyl), 5-(quinolin-5-yl-amino-carbonyl), 5-(quinolin-6-yl-amino-carbonyl), 5-(isoquinolin-5-yl-amino-carbonyl), 5-(isoquinolin-8-yl-amino-carbonyl), 5-(pyrid-3-yl), 5-(pyrid-4-yl), 5-(6-methoxy-pyrid-3-yl), 5-(2,3-dihydro-benzo[b][1,4]dioxin-6-yl) and 5-(benzo[d][1,3]dioxol-5-yl);

and wherein the starred stereo-center is present in an enantiomeric excess of the (S)-stereo-configuration;

or a pharmaceutically acceptable salt thereof.

8. A compound as in claim 4, wherein

R¹ is thien-2-yl; n is 1; L is selected from the group consisting of

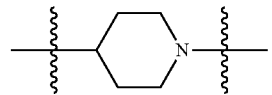

and —CH₂CH₂CH₂—NH—; Y is CH; and X is NH; R² is selected from the group consisting of 5-(3,4-dimethoxyphenyl) and 5-(3,4-dimethoxyphenyl-amino-carbonyl); and wherein the starred stereo-center is present in an enantiomeric excess of the (S)-stereo-configuration;

or a pharmaceutically acceptable salt thereof.

9. A compound as in claim 1, wherein the starred stereo-center is present in an enantiomeric excess of the (S)-stereo-configuration.

10. A pharmaceutical composition comprising a pharmaceutically acceptable carrier and a compound of claim 1.

11. A pharmaceutical composition made by mixing a compound of claim 1 and a pharmaceutically acceptable carrier.

12. A process for making a pharmaceutical composition comprising mixing a compound of claim 1 and a pharmaceutically acceptable carrier.

13. A method of treating rheumatoid arthritis, asthma, chronic obstructive pulmonary disease, sepsis, irritable bowel disease, cystic fibrosis, or abdominal aortic aneurism in a subject in need thereof comprising administering to the subject a therapeutically effective amount of the composition of claim 10.

14. A method of treating a disorder selected from the group consisting of rheumatoid arthritis, asthma, chronic obstructive pulmonary disease, sepsis, irritable bowel disease, cystic fibrosis, and abdominal aortic aneurism comprising administering to a subject in need thereof a therapeutically effective amount of the compound of claim 1.

15. A compound of formula (II)

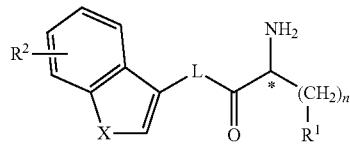

(II)

wherein

R$^1$ is selected from the group consisting of C$_{1-4}$alkyl, —C(O)—NH$_2$, C$_{3-6}$cycloalkyl, phenyl and 5 to 6 membered heteroaryl; wherein the heteroaryl is optionally substituted with one or more substituents independently selected from halogen and C$_{1-4}$alkyl;

n is an integer from 0 to 1;

L is selected from the group consisting of —CH$_2$CH$_2$—NR$^A$— and —CH$_2$CH$_2$CH$_2$—NR$^A$—; wherein R$^A$ is selected from the group consisting of hydrogen, methyl and ethyl;

X is selected from the group consisting of N(R$^B$), O and S; wherein R$^B$ is selected from the group consisting of hydrogen and C$_{1-4}$alkyl;

R$^2$ is selected from the group consisting of hydrogen, halogen, nitro, —CO$_2$H, —C(O)—NR$^C$R$^D$, -Q, —O-Q and —C(O)—NH-Q;

wherein R$^C$ and R$^D$ are each independently selected from the group consisting of hydrogen and C$_{1-4}$alkyl; alternatively, R$^C$ and R$^D$ are taken together with the nitrogen atom to which they are bound to form a ring structure selected from the group consisting of piperidin-1-yl, piperazin-1-yl, pyrrolidin-1-yl, morpholin-4-yl, 1,2,3,4-tetrahydroquinolin-1-yl and 1,2,3,4-tetrahydro-isoquinolin-2-yl;

wherein Q is selected from the group consisting of aryl, aralkyl, heterocyclyl, benzo[d][1,3]dioxolyl and 2,3-dihydro-benzo[b][1,4]dioxinyl;

wherein the aryl or heterocyclyl, whether alone or as part of a substituent group, is optionally substituted with one or more substituents independently selected from the group consisting of halogen, cyano, C$_{1-4}$alkyl, halogenated C$_{1-4}$alkyl, C$_{1-4}$alkoxy, halogenated C$_{1-4}$alkoxy, —CO$_2$H, —C(O)—NR$^E$R$^F$, —SO$_2$—NR$^E$R$^F$ and phenyl; wherein R$^E$ and R$^F$ are each independently selected from the group consisting of hydrogen and C$_{1-4}$alkyl;

and wherein the heterocyclyl contains one or more S heteroatoms, said heterocyclyl may be further optionally substituted on said one or more S heteroatoms with one to two oxo groups;

or a pharmaceutically acceptable salt thereof.

16. A compound as in claim 15, wherein

R$^1$ is selected from the group consisting of C$_{1-4}$alkyl, —C(O)—NH$_2$, C$_{4-6}$cycloalkyl and 5 to 6 membered heteroaryl; wherein the 5 to 6 membered heteroaryl is optionally substituted with a substituent selected from the group consisting of halogen and C$_{1-4}$alkyl;

n is an integer from 0 to 1;

L is selected from the group consisting of —CH$_2$CH$_2$—NR$^A$— and —CH$_2$CH$_2$CH$_2$—NR$^A$—; wherein R$^A$ is selected from the group consisting of hydrogen, methyl and ethyl;

X is selected from the group consisting of N(R$^B$), O and S; wherein R$^B$ is selected from the group consisting of hydrogen and C$_{1-4}$alkyl;

R$^2$ is selected from the group consisting of hydrogen, halogen, nitro, carboxy, phenyl, —O-phenyl, —C(O)—NR$^C$R$^D$ and —C(O)—NH-Q;

wherein R$^C$ and R$^D$ are each independently selected from the group consisting of hydrogen and C$_{1-2}$alkyl; alternatively, R$^C$ and R$^D$ are taken together with the nitrogen atom to which they are bound to form a ring structure selected from the group consisting of piperidin-1-yl, pyrrolidin-1-yl, 1,2,3,4-tetrahydroquinolin-1-yl and 1,2,3,4-tetrahydro-isoquinolin-2-yl;

wherein Q is selected from the group consisting of phenyl, naphthyl, —C$_{1-2}$alkyl-phenyl, heterocyclyl, benzo[d][1,3]dioxolyl and 2,3-dihydro-benzo[b][1,4]dioxinyl;

wherein the phenyl or heterocyclyl, whether alone or as part of a substituent group, is optionally substituted with one to two substituents independently selected from the group consisting of halogen, cyano, C$_{1-4}$alkyl, fluorinated C$_{1-2}$alkyl, C$_{1-4}$alkoxy, fluorinated C$_{1-2}$alkoxy, —CO$_2$H, —C(O)NH$_2$, —SO$_2$—NH$_2$ and phenyl;

and wherein the heterocyclyl contains one or more S heteroatoms, said heterocyclyl may be further optionally substituted on said one or more S heteroatoms with one to two oxo groups;

or a pharmaceutically acceptable salt thereof.

17. A compound as in claim 16, wherein

R$^1$ is C$_{1-4}$alkyl; n is 0; X is selected from the group consisting of N(R$^B$) and S; wherein R$^B$ is selected from the group consisting of hydrogen and C$_{1-2}$alkyl; and R$^2$ is hydrogen;

or a pharmaceutically acceptable salt thereof.

18. A compound as in claim 17, wherein

R$^1$ is ethyl; n is 0; X is selected from the group consisting of NH and S; and R$^2$ is hydrogen; and wherein the starred stereo-center is present in an enantiomeric excess of the (S)-stereo-configuration;

or a pharmaceutically acceptable salt thereof.

19. A compound as in claim 15, wherein the starred stereo-center is present in an enantiomeric excess of the (S)-stereo-configuration.

20. A pharmaceutical composition comprising a pharmaceutically acceptable carrier and a compound of claim 15.

21. A pharmaceutical composition made by mixing a compound of claim 15 and a pharmaceutically acceptable carrier.

22. A process for making a pharmaceutical composition comprising mixing a compound of claim 15 and a pharmaceutically acceptable carrier.

23. A method of treating rheumatoid arthritis, asthma, chronic obstructive pulmonary disease, sepsis, irritable bowel disease, cystic fibrosis, or abdominal aortic aneurism in a subject in need thereof comprising administering to the subject a therapeutically effective amount of the composition of claim 20.

24. A method of treating a disorder selected from the group consisting of rheumatoid arthritis, asthma, chronic obstructive pulmonary disease, sepsis, irritable bowel disease, cystic fibrosis, and abdominal aortic aneurism comprising administering to a subject in need thereof a therapeutically effective amount of the compound of claim 15.

* * * * *